United States Patent [19]

Theeuwes

[11] 4,256,108
[45] * Mar. 17, 1981

[54] MICROPOROUS-SEMIPERMEABLE LAMINATED OSMOTIC SYSTEM

[75] Inventor: Felix Theeuwes, Los Altos, Calif.

[73] Assignee: Alza Corporation, Palo Alto, Calif.

[*] Notice: The portion of the term of this patent subsequent to Jul. 10, 1996, has been disclaimed.

[21] Appl. No.: 34,275

[22] Filed: May 21, 1979

Related U.S. Application Data

[63] Continuation-in-part of Ser. No. 785,582, Apr. 7, 1977, Pat. No. 4,160,452.

[51] Int. Cl.³ .............................................. A61M 7/00
[52] U.S. Cl. .................................................. 128/260
[58] Field of Search ...................... 128/213 R, 260–261

[56] References Cited

U.S. PATENT DOCUMENTS

| | | | |
|---|---|---|---|
| 3,948,254 | 4/1976 | Zaffaroni ............................ | 128/260 |
| 4,036,227 | 7/1977 | Zaffaroni et al. .................... | 128/260 |
| 4,135,514 | 1/1979 | Zaffaroni et al. .................... | 128/260 |
| 4,160,452 | 7/1979 | Theeuwes ............................ | 128/260 |

*Primary Examiner*—Robert W. Michell
*Assistant Examiner*—C. F. Rosenbaum
*Attorney, Agent, or Firm*—Paul L. Sabatine; Thomas E. Ciotti; Edward L. Mandell

[57] ABSTRACT

An osmotic therapeutic system for delivering a drug is disclosed. The system comprises a drug delivery module which module comprises a rate controlling laminated wall surrounding a reservoir and has a portal for delivering drug from the system. The laminated wall comprises a semipermeable lamina in laminar arrangement with a microporous lamina to provide a wall that is permeable to an external fluid, impermeable to drug and maintains its integrity during the delivery of drug. The reservoir contains a drug, or a mixture of drug and a solute which drug or solute is soluble in the fluid and exhibits an osmotic pressure gradient across the wall against the fluid. In operation, drug is released from the system by fluid being imbibed through the wall into the reservoir at a rate determined by the permeability of the wall and the osmotic pressure gradient across the wall thereby producing a solution of drug, or a solution of solute containing drug which solution is released through the portal at a controlled rate over a prolonged period of time.

66 Claims, 13 Drawing Figures

FIG. 8
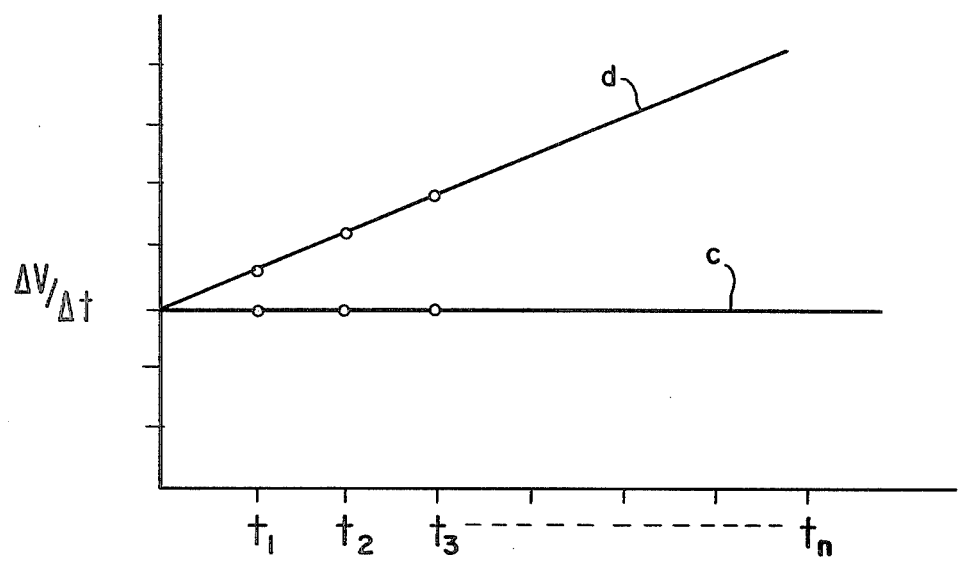
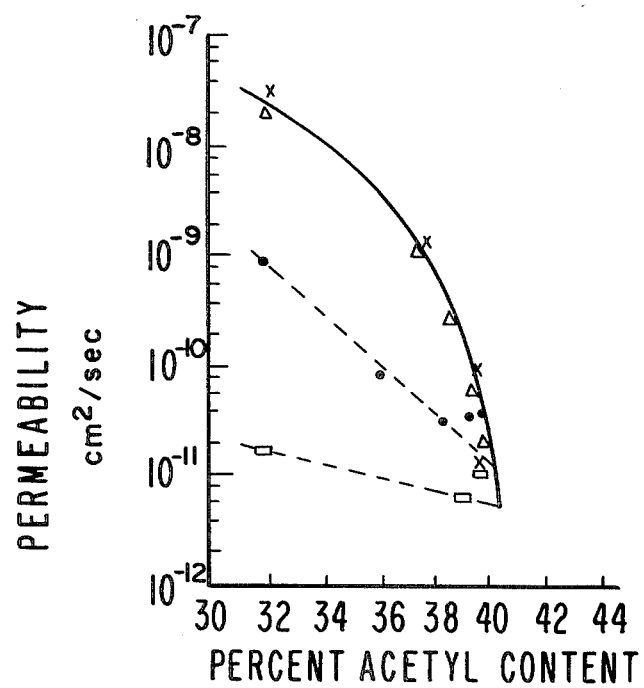
FIG. 9

MICROPOROUS-SEMIPERMEABLE LAMINATED OSMOTIC SYSTEM

CROSS-REFERENCE TO RELATED APPLICATION

This application is a continuation-in-part of copending application United States Ser. No. 785,582 filed on Apr. 7, 1977, and now U.S. Pat. No. 4,160,452 issued on July 10, 1979, by inventor Felix Theeuwes. Application Ser. No. 785,582 is incorporated herein by reference, and benefit is claimed on its filing date. Application Ser. No. 785,582 and this application are both assigned to the Alza Corporation of Palo Alto, California.

FIELD OF THE INVENTION

This invention pertains to a therapeutic osmotic system that is a controlled dosage form. The therapeutic osmotic system provides pre-programmed, unattended delivery of drug at a rate, and for a time period, established to meet a specific therapeutic need. The system is manufactured in the form of a device for delivering drug to a selected drug receptor site.

BACKGROUND OF THE INVENTION

Osmotic therapeutic systems manufactured in the form of osmotic devices for the precision administration of drugs with control of delivery patterns and with extended operational delivery times are known in U.S. Pat. No. 3,845,770 and 3,916,899. The systems disclosed in these patents are made of a single layer wall that surrounds a reservoir containing a drug. The wall is permeable to the passage of an external fluid, impermeable to the passage of drug, and it has a portal for delivering drug from the system. Those systems are extraordinarily effective for delivering a drug that is soluble in the fluid, and also for delivering a drug that has limited solubility in the fluid and is mixed with an osmotically effective compound that is soluble in the fluid and exhibits an osmotic pressure gradient across the wall against the fluid. The systems release drug by fluid imbibed through the wall into the reservoir at a rate determined by the permeability of the wall and the osmotic pressure gradient across the wall producing a solution of soluble drug, or a solution of soluble compound containing drug which solution in either operation is dispensed at a controlled rate over a prolonged period of time. While the above systems represent an outstanding and pioneer advancement in the osmotic art, and while they are useful for dispensing innumerable drugs to the environment of use, it has now been found these osmotic systems can have a unique laminated wall that unexpectedly improves the usefulness and the integrity of the systems.

That is, the systems of this invention for example, comprise in one embodiment a unique laminated wall having a thin lamina formed of a material possessing a given set of properties in laminar arrangement with a supporting, preferably thicker lamina possessing a different set of properties. A system embracing a laminated structure made according to the present invention can have properties such as permeability to external fluid, impermeability to drugs and solutes, and physical and chemical integrity be selected independently, and also have the mode and manner of drug release be made programmable based on the laminae comprising the structured, laminated wall. For example, the wall can comprise a laminae consisting of a thin to very thin lamina facing the environment and a thicker supporting lamina facing the reservoir with each possessing different properties. The lamina facing the environment can be made of a semipermeable material permeable to fluid, impermeable to drug, and inert in the presence of drug and by being made thin to very thin the lamina allows for an increase in the delivery rate. The lamina facing the reservoir can be made of a microporous material selected to exhibit a low to zero resistance to the passage of fluid compared to the semipermeable lamina, which microporous lamina also provides structural support for the semipermeable lamina and does not interact with drug and fluid. The orientation of the laminae comprising the laminated wall can also embrace the reserve structure of the just-described wall. In this laminated structure, the microporous lamina faces the environment of use, and the entrance of drug from the reservoir into the micropores of the lamina is avoided by having the semipermeable lamina of the laminate facing the reservoir. The structure of the laminated wall allows the use of more inert, polymeric lamina materials which are usually less permeable to fluid. The invention's use of a thin rate controlling semipermeable lamina assures that a sufficiently high rate of drug release can be maintained when needed from the system. The therapeutic systems made available by this invention and embodying the unique laminated wall thereby functions according to a pre-selected built-in optimal program of drug presentation.

OBJECTS OF THE INVENTION

Accordingly, it is an immediate object of this invention to provide an improved osmotic therapeutic system for the controlled delivery of a drug to a drug receptor site over a prolonged period of time.

Another object of the invention is to provide an osmotic system comprising a laminated wall formed of at least two laminae each made of different materials which materials maintain their physical and chemical integrity during the controlled dispensing of drug over a prolonged period of time.

Yet another object of the invention is to provide an osmotic system comprising a laminated wall comprising a semipermeable lamina and a microporous lamina which laminae act in cooperation to provide improved control delivery of drug.

Still a further object of the invention is to provide an osmotic system having laminated walls in which properties such as fluid transmission rates and resistance to attack by the drug may be independently controlled and regulated for a particular application and environment of use.

Yet still another object of the invention is to provide an osmotic system having a laminated wall that has a programmable flux rate to fluids, a high degree of exclusion towards drugs and a resistance to hydrolysis over a wide pH range in the presence of drug and biological fluids.

Yet still another object of the invention is to provide an osmotic system for administering drug where the dose administered contains the intended quantity and is administered at a useful rate to ensure the required onset, intensity and duration of biological response.

Still another object of the invention is to provide an osmotic system having a laminated wall comprising laminae of different thickness which makes the system programmable and versatile, and allows a wider control over the rate drug is released to a drug receptor site.

Other objects, features and advantages of the invention will be more apparent to those skilled in the art from the following detailed specification, taken in conjunction with the drawings and the accompanying claims.

STATEMENT OF THE INVENTION

This invention concerns an osmotic system for dispensing a drug. The system comprises a laminated wall surrounding a reservoir and has a portal for dispensing drug. The compartment contains a drug that is soluble in an external fluid and exhibits an osmotic pressure gradient across the wall against the fluid, or the reservoir contains a mixture of drug having a limited solubility in the fluid and an osmotically effective solute soluble in fluid that exhibits an osmotic pressure gradient across the wall against the fluid. The wall is permeable to fluid, impermeable to drug and solute, and chemically inert towards drug, solute and the environment of use. The wall is formed of a semipermeable lamina laminated to a microporous lamina. Drug is released from the system by fluid being imbibed through the laminated wall into the reservoir at a rate controlled by the wall and the pressure gradient across the wall producing a solution containing agent that is released through the portal at a controlled rate over a prolonged period of time.

BRIEF DESCRIPTION OF THE DRAWINGS

In the drawings, which are not shown to scale, but are set forth to illustrate various embodiments of the invention, the figures are as follows:

FIG. 8 is a graph comparing the fluid flux through a semipermeable lamina, identified as c, that maintains its integrity in the presence of fluid with a semipermeable lamina, identified as d, that slowly loses its integrity in the presence of fluid;

FIG. 9 is a graph representing the permeability of a series of semipermeable lamina to a series of osmotic solutes;

In the drawings and specification, like parts in related figures are identified by like numbers. The terms appearing earlier in the specification and in the description of the drawings, as well as embodiments thereof, are further detailed in the disclosure.

DETAILED DESCRIPTION OF THE DRAWINGS

Figure 1:
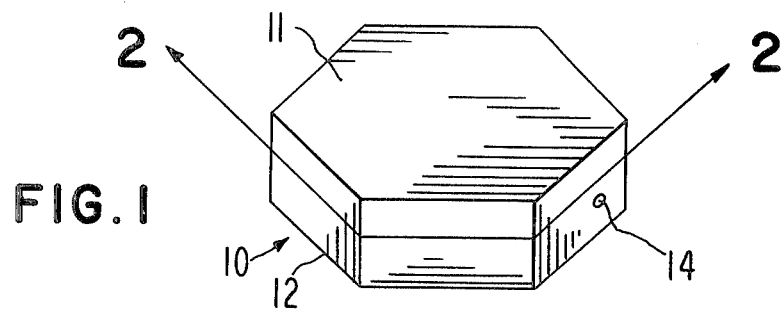
FIG. 1 is a view of an osmotic therapeutic system designed for orally delivering a beneficial drug.
Figure 2:
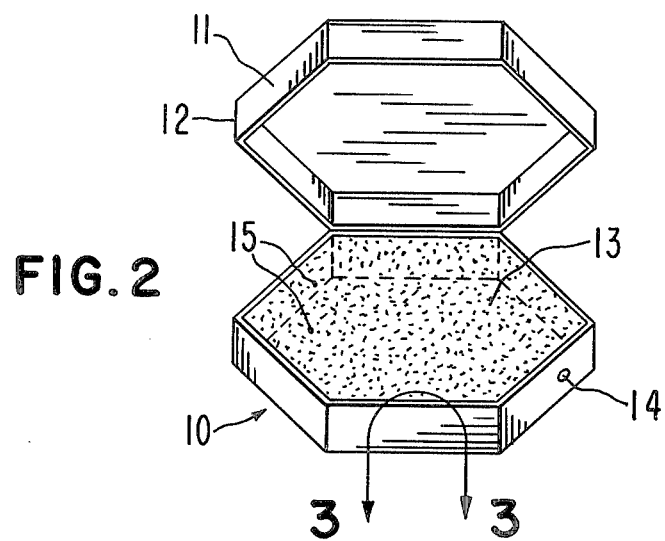
FIG. 2 is a view of the osmotic system of FIG. 1 in opened section through 2—2 illustrating the reservoir of the system.
Figure 3:
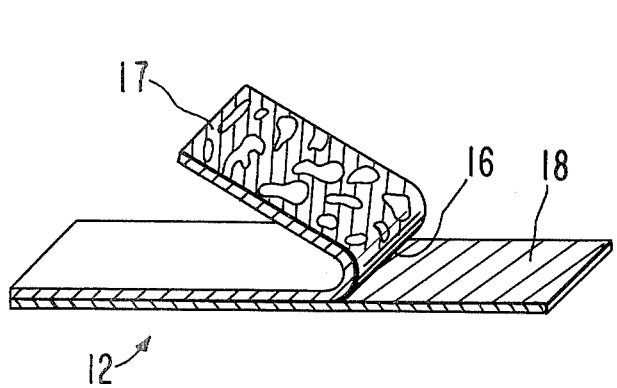
FIG. 3 is a view of a section through 3—3 of the laminated wall of the osmotic system of FIG. 2 illustrating the laminated wall of the system.

Turning now to the drawings in detail, which are examples of various osmotic systems of the invention, and which examples are not to be construed as limiting, one embodiment of an osmotic system as indicated in FIGS. 1, 2 and 3 considered together by the numeral 10. In FIGS. 1, 2 and 3 an osmotic system 10 is made in the form of an oral, osmotic therapeutic system and it is comprised of a body 11 having a laminated wall 12 that surrounds a reservoir 13, or compartment, seen in FIG. 2 in opened section through 2—2 of FIG. 1. System 10 has a portal 14, or passageway, in laminated wall 12 that extends through 12 and communicates with reservoir 13 and the exterior of system 10. Reservoir 13, as seen in FIG. 2, is a means for containing a beneficial agent, identified by dot 15, preferably a drug, that is soluble in an external fluid and exhibits an osmotic pressure gradient across 12 against an external fluid, or reservoir 13 optionally contains a mixture of agent 15 having limited solubility in the fluid along with an osmotically effective solute, not seen in FIG. 2, that is soluble in the fluid and exhibits an osmotic pressure gradient across wall 12. Reservoir 13 optionally contains a non-toxic dye for identifying agent 15 and for making release of agent 15 visible to the unaided eye.

Laminated wall 12, as seen in FIG. 3, represents a section through 3—3 removed from wall 12 of system 10 of FIG. 2. Laminated wall 12 is separated at 16 for illustrating the laminae forming the structure of wall 12. Wall 12 comprises a lamina 17 formed of a microporous material and a lamina 18 formed of a semipermeable material. In one operative embodiment, lamina 17 is the interior lamina of wall 12 facing reservoir 13 with lamina 17 functioning as a support or rigid structure for lamina 18. Lamina 17 exhibits low to zero resistance to the passage of fluid and it is substantially free of drug membrane interaction. In the described structure, when lamina 17 faces reservoir 13, with lamina 17 housing a microporous pore-former, described hereinafter, microporous lamina 17 is formed in situ during operation of system 10. Microporous lamina 17 is formed by fluid imbibed through semipermeable lamina 18 with accompanying wetting and dissolving the pore-former, which then leave lamina 17 under the influence of inward imbibition pressure and continuous inward fluid movement. These combined processes form microporous lamina 17 during operation of system 10. In this embodiment, lamina 18 is the exterior lamina of wall 12 facing the environment, distant from reservoir 13, and is the rate controlling lamina of wall 12. Lamina 18 is permeable to the passage of fluid, impermeable to the passage of agent, drug and solute, it maintains its physical and chemical integrity in the environment of use, and it is more particularly substantially non-erodible and inert in the environment.

In another embodiment laminated wall 12 can be manufactured with the microporous lamina 17 facing the environment of use distant from reservoir 13. In this structure, semipermeable lamina 18 is the interior lamina facing reservoir 13. When lamina 17 faces the environment of use, 17 can be a preformed microporous material or 17 can house microporous pore-formers that are wettable, dissolvable and removed by the fluid in the environment, thereby forming microporous lamina 17 during operation of system 10. Lamina 18 for this system and other systems can be formed of a single semipermeable material, or lamina 18 is a composite comprising at least two semipermeable wall forming materials. The composite semipermeable lamina is (a) permeable to the passage of an external fluid, (b) substantially impermeable to the passage of drug, agents and solute in the reservoir, (c) maintains its physical and chemical integrity in the presence of agent, drug and fluid, (d) is substantially non-erodible and inert, and (e) can be made thin to very thin while simultaneously controlling the permeability to fluid for imbibition by the system. A detailed description of laminae-forming materials, agents and compounds is presented later in the specification.

In operation, system 10 releases agent or drug 15 contained in reservoir 13 and soluble in the external fluid by fluid being imbibed into reservoir 13 in a tendency towards osmotic equilibrium at a rate controlled by the permeability of laminated wall 12 and the osmotic pressure gradient across laminated wall 12 to continuously dissolve agent 15 which is osmotically pumped from system 10 through passageway 14 at a controlled and continuous rate over a prolonged period of time. System 10, also releases agent 15 that has limited solubility in the fluid and is mixed with an osmotically effective compound by fluid being imbibed through laminated wall 12 into reservoir 13 in a tendency towards osmotic equilibrium at a rate controlled by the permeability of wall 12 and the osmotic pressure gradient across wall 12, to continuously dissolve the osmotically effective compound and form a solution containing agent that is released from system 10 through passageway 15 at a controlled and continuous rate over a prolonged period of time.

Osmotic system 10 of FIGS. 1 through 3 can be made into many useful embodiments including the presently preferred embodiment for oral use. The oral system is useful for releasing in the gastrointestinal tract either a locally or systematically acting agent over a prolonged period of time. Osmotic, oral therapeutic system 10 can have various conventional shapes and sizes such as round with a diameter of 3/16 inches to ½ inches, or it can be shaped like a capsule having a range of sizes from triple zero to zero, and from 1 to 8.

Figure 4:
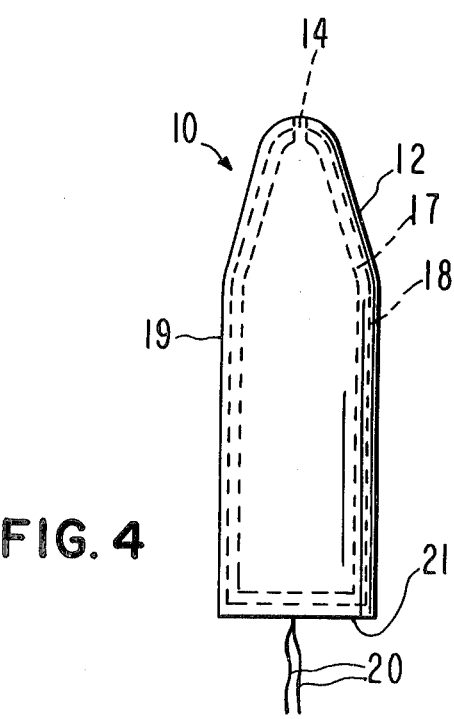
FIG. 4 is a view of an osmotic therapeutic system manufactured for administering drug in the vagina.

FIG. 4 represents another osmotic therapeutic system 10 manufactured according to the invention for administering drug to drug receptor. In the illustrated embodiment, system 10 is designed for placement and drug release in the vagina, not shown. System 10 has a conically-shaped body 19 with a string 20 attached thereto for removing system 10 from the vaginal vault. System 10 is made with a base 21 big enough to contact, when system 10 is placed in a vagina, the surrounding mucous tissues of the vagina. System 10 comprises a portal 14 and is formed with a laminated wall 12 comprising a microporous lamina 17 and a semipermeable lamina 18. System 10 operates as above described and it is sized, shaped and adapted for placement in the vagina for releasing a drug including contraceptives in the vagina.

Figure 5:
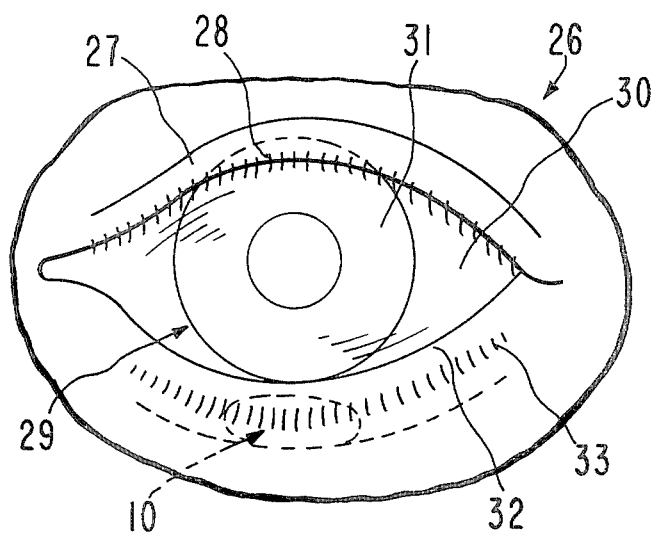
FIG. 5 is a front view of the human eye illustrating an ocular osmotic system positioned in the eye.

Referring to FIG. 5, an ocular therapeutic system 10 is seen in eye 26 for administering drug at an osmotically metered dosage rate thereto. In FIG. 5, eye 26 is comprised of an upper eyelid 27 with eyelashes 28, a lower eyelid 32 with eyelashes 33, and an eyeball 29 covered for the greater part by sclera 30 and at its center area by cornea 31. Eyelids 27 and 32 are lined with an epithelial membrane or palpebral conjunctiva, sclera 30 is lined with a bulbar conjunctiva that covers the exposed surface of eyeball 29, and cornea 31 is covered with a transparent epithelial membrane. The portion of the conjunctiva which lines upper eyelid 27 and the underlying portion of the bulbar conjunctiva defines an upper cul-de-sac, while that portion of the palpebral conjunctiva which lines the lower eyelid 35 and the underlying portion of the bulbar conjunctiva defines a lower cul-de-sac. Ocular osmotic system 10, seen in broken lines, is shaped, sized and adapted for placement in the upper or lower cul-de-sac. System 10 is seen in the lower cul-de-sac and it is held in place by the natural pressure of lower eyelid 32. System 10 contains an opthalmic drug for release to eye 26 at a controlled and continuous rate over a prolonged period of time.

Ocular system 10 can have any geometric shape that fits comfortably in the cul-de-sac. Typical shapes include bean, banana, circular, rectangular, crescent, and half-ring shaped systems. In cross-section, the system can be doubly convex, concavo-convex, and the like, as the device will in use tend to conform to the shape of the eye. The dimensions of an ocular system can vary widely with the lower limit governed by the amount of drug to be supplied to the eye as well as by the smallest sized system that can be placed into the eye. The upper limit on the size of the system is governed by the space limitation in the eye consistent with comfortable retention in the eye. Satisfactory systems generally have a length of 4 to 20 millimeters, a width of 1 to 15 millimeters, and a thickness of 0.1 to 4 millimeters. The ocular system can contain from 0.15 micrograms to 100 milligrams of drug, or more, and it is made from non-erodible and inert materials that are compatible with the eye and its environment.

Figure 6:
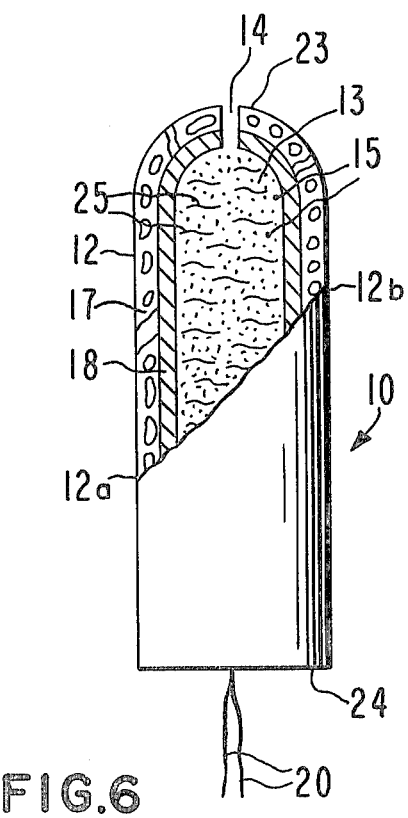
FIG. 6 is a view of an osmotic therapeutic system manufactured for administering drug in the anus with the system seen in opened section for elucidating structural details thereof.
Figure 7:
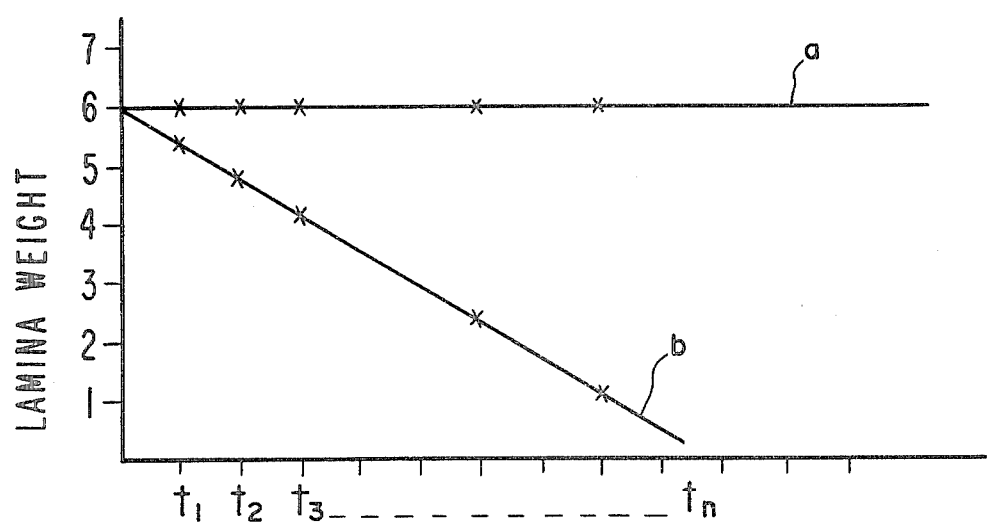
FIG. 7 is a graph comparing a semipermeable lamina, identified as a, that is inert, with a semipermeable lamina, identified as b, that slowly loses its integrity in the presence of agent solution.

FIG. 6 illustrates another osmotic therapeutic system 10 designed for administering a locally or systemically acting drug within a body opening, the anal-rectal canal, not shown. System 10 is shaped like an obelisk having a lead end 23, a rear end 24, and it is equipped with a string 20 for removing the system from the body. System 10 comprises a laminated wall 12 seen in opened section at 12a to 12b which wall 12 surrounds a reservoir 13 containing drug 15. Drug 15 is soluble in external fluid or it has limited solubility in the fluid and it is optionally mixed with an osmotically effective solute 25 that exhibits an osmotic pressure gradient across wall 12 against external fluid. The osmotic solute also can have properties 1 and 2 as listed supra. System 10 has a delivery portal 14 for releasing drug 15 from system 10 to the anal-rectal environment. Laminated wall 12 is formed of a pair of laminae 17 and 18 surrounding and forming reservoir 13. In the embodiment illustrated in FIG. 6, lamina 17 is positioned distant from reservoir 13 and lamina 18 is positioned adjacent to reservoir 13. System 10 operates in the manner described above.

While FIGS. 1 through 6 are illustrative of various osmotic systems 10 that can be made according to the invention, it is to be understood these systems are not to be construed as limiting, as the systems can take a wide variety of shapes, sizes and forms adapted for delivering agent to different environments of use. For example, the systems include buccal, implant, topical, nose, artificial gland, rectum, cervical, intrauterine, arterial, venous, ear, and the like biological environments. The systems also can be adapted for delivering an active agent in streams, aquariums, fields, factories, reservoirs, laboratory, facilities, hot houses, transportation means, naval means, air and military means, hospitals, verterinary clinics, nursing homes, chemical reactions and other environments of use.

DETAILED DESCRIPTION OF THE INVENTION

In accordance with the practice of this invention, it has now been found that osmotic system 10 can be successfully manufactured with a laminated wall 12 comprising two different laminae in laminar arrangement that act in concert to form an integral unit wall 12, which laminate 12 maintains its physical and chemical integrity and does not separate into lamina throughout the operative agent release history of osmotic system 10.

Further, in accordance with the practice of the invention, it has been discovered laminated wall 12 can be made in operative embodiment comprising a semipermeable lamina 18 which 18 comprises (a) a single semipermeable lamina forming material, or (b) a semipermeable lamina formed of a blend of semipermeable lamina forming materials, which semipermeable lamina 18 in either (a) or (b) is in intimate laminar arrangement with a microporous lamina 17 formed of a microporous material. Materials suitable for forming semipermeable lamina 18, when it is made of a single material, are generally polymeric materials. The polymeric materials are homopolymers and copolymers, and they include semipermeable, osmosis and reverse osmosis materials. The semipermeable materials are independently selected from semipermeable homopolymers and semipermeable copolymers which generically include polysaccharides comprising anhydroglucose units. In one embodiment, the polysaccharides are cellulose and esters and ethers, and mixed esters and ethers having a degree of substitution, D.S., on the anhydroglucose unit from greater than 0 up to 3 inclusive. By "degree of substitution" as used herein is meant the average number of hydroxyl groups on the anhydroxyl groups on the anhydroglucose unit of the polymer replaced by a substituting group. Lamina 18 can consist of a single semipermeable polymeric lamina forming polymer, such as polymeric acylated cellulose, or 18 can consist of two or more polymeric lamina forming polymers, for example, a polymeric acylated cellulose and a different polymeric cellulose substitute with different groups.

Materials suitable for forming semipermeable lamina 18 include polymeric cellulose esters and ethers and copolymeric cellulose esters and ethers. These include, polymeric acylated cellulose, which are cellulose polymers having at least one acyl group, for example, mono, di and tricellulose acylates. Exemplary polymers include cellulose acetate having a D.S. up to 1 and acetyl content up to 21%; cellulose diacetate having a D.S. of 1 to 2 and an acetyl content of 21 to 35%; cellulose triacetate having a D.S. of 2 to 3 and an acetyl content of 35 and 44.8%; cellulose propionate having an acetyl content of 1.5 to 7% and a propionyl content content of 2.5 to 3% and an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate having an acetyl content of 2 to 29.5%, a butyryl content of 17 to 53%, and a hydroxyl content of 0.5 to 4.7%; cellulose triaceylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydrolysis of the corresponding triester to yield cellulose diacylates having a D.S. of 2.2 to 2.6 such as cellulose dicaprylate and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional semipermeable lamina forming material that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methylcellulose acetate methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose sterate, cellulose acetate methylcarbamate, acylated polysaccharides, acylated starches, aromatic nitrogen containing polymeric materials that exhibit permeability to aqueous fluids and substantially no passage to solute, semipermeable membranes made from polymeric epoxides, copolymers of alkylene oxides and alkyl glycidyl ethers, semipermeable polyurethanes, and the like. In the embodiment when semipermeable lamina 18 consists of two semipermeable lamina forming polymers that act together and functions as the equivalent of a single semipermeable lamina, the polymers are different and independently selected from those set-forth above. For this lamina, the two polymers are selected from the group consisting of cellulose, cellulose substituted with non-acrylated groups, cellulose acylate, cellulose diacylate and cellulose triacylates, and in presently preferred embodiment one of the cellulose polymers selected exhibits a higher percent substitution of the acyl moiety when both polymers have an acyl group.

Generally, semipermeable materials for forming the lamina will have a fluid permeability of $10^{-5}$ to $10^{-1}$ (cc mil/cm$^2$hr atm), expressed per atmosphere (atm) of hydrostatic or or osmotic pressure difference across wall 12 or lamina 18 at the temperature of use while possessing a high degree of impermeability to solute are useful for the purpose of the invention. The polymers described are known to the art or they can be prepared according to the procedures in *Encyclopedia of Polymer Science and Technology*, Vol. 3, pages 325 to 354, and 459 to 549, published by Interscience Publishers, Inc., New York, in *Handbook of Common Polymers* by Scott, J. R. and Roff, W. J., 1971, published by CRC Press, Cleveland, Ohio; and in U.S. Pat. Nos. 3,133,132; 3,173,876; 3,276,586; 3,541,055; 3,541,006; and 3,546,142.

Further, in accordance with the invention, lamina 18 when formed of more than one material consists of, (1) at least one semipermeable lamina forming material permeable to the passage of fluid and substantially impermeable to the passage of drug and solute, and other lamina forming polymers and compounds uniformly blended with at least one or more of the following lamina forming materials, (2) a semipermeable polymer that aids in controlling the fluid flux of the semipermeable lamina, and also functions as a stabilizing material that imparts physical and chemical integrity to lamina 18, and more particularly gives lamina 18 inertness toward agents including drugs, compounds and solutions thereof and to compounds and solutions present in the environment of use, (3) a flux regulator that aids in governing the permeability of fluid through the lamina, (4) a plasticizer that gives flexibility to the lamina, and (5) a dispersant useful for forming the materials into the operative, integral composite semipermeable lamina 18.

The semipermeable polymer homogenously compounded with a different semipermeable polymer which latter polymer is used to make lamina 18, is for the former polymer, a polymer that aids in defining the physical and chemical properties of lamina 18 such that lamina 18 operates and functions as though it consists essentially of a single entity. For this embodiment, a suitable semipermeable material can be selected from the above semipermeable materials for blending with a semipermeable lamina forming material by using the following scientific criterions: (a) the material selected possesses a high degree of substitution, for example, the material has undergone etherification or esterification particularly acylation towards or to completion for forming a lamina that demonstrates increased resistance to hydrolysis and increased rejection of agent, (b) the semipermeable polymer exhibits a flux decrease to fluid and solute with increasing molecular size of the substituting group on the polymer, (c) the semipermeable polymer exhibits a flux decrease proportional to the increase in size of the substituent, for example, the decrease occurs as the number of carbon atoms increase in a hydrocarbon moiety such as an alkyl or alkoxy moiety, (d) the semipermeable polymer exhibits increased stability with an increase in the degree of substitution of hydrophobic ether and larger hydrophobic ester groups with an accompanying decrease in the degree of substitution of smaller hydrophilic ester groups, and (e) the semipermeable polymer exhibits a flux decrease as the number of polar, and ionic groups bonded to the polymer decrease. These principles are exemplified and illustrated in FIG. 9. FIG. 9 is an illustration of the decrease in polymer permeability to solutes such as sodium chloride indicated by X, potassium chloride indicated by $\Delta$, magnesium sulfate indicated by $\square$, and potassium sulfate indicated by o, with increasing degrees of substitution by ester groups including acetyl moieties. A lower permeability to solute signifies a higher rejection or exclusion of the solute from the polymer network, thereby diminishing the chance for polymer-solute interaction. The trends shown in FIG. 9 for the indicated solutes hold for other agents. Generally, the amount of semipermeable polymer used will range from 1 to 50 percent on the total weight of semipermeable lamina 18. Procedures useful from measuring fluid permeability and osmotic flow are disclosed in *J. App. Poly. Sci.*, Vol. 9, pages 1341 to 1362; and in *Yale J. Biol. Med.*, Vol. 42, pages 139 to 153, 1970.

The expressions "flux regulator agent," "flux enhancing agent" and "flux decreasing agent" as used herein means a compound that when added to semipermeable lamina forming material assists in regulating the fluid permeability of flux through the semipermeable lamina. The agent can be preselected to increase or decrease the liquid flux. Agents that produce a marked increase in permeability to fluid such as water, are often essentially hydrophilic, while those that produce a marked decrease to fluids such as water, are essentially hydrophobic. The flux regulators in some embodiments also can increase the flexibility of the lamina. The flux regulators in one embodiment, are polyhydric alcohols and derivatives thereof, such as polyalkylene glycols of the formula H-(O-alkylene)n-OH wherein the bivalent alkylene radical is straight or branched chain and has from 1 to 10 carbon atoms and n is 1 to 500 or higher. Typical glycols include polyethylene glycols 300, 400, 600, 1500, 1540, 4000 and 6000 of the formula H—$(OCH_2CH_2)_n$—OH wherein n is respectively 5 to 5.7, 8.2 to 9.1, 12.5 to 13.9, 29 to 36, 29.8 to 37, 68 to 84, and 158 to 204. Other polyglycols include the low molecular weight glycols such as polypropylene, polybutylene and polyamylene.

The flux regulators in another emobidment include poly($a,\omega$)alkylenediols wherein the alkylene is straight or branched chain of from 2 to 10 carbon atoms such as poly(1,3)propanediol, poly(1,4)butanediol, poly(1,5-)pentanediol and poly(1,6)hexanediol . . . The diols also include aliphatic diols of the formula $HOC_nH_{2n}OH$ wherein n is from 2 to 10 and the diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux regulators include esters and polyesters of alkylene glycols of the formula HO—(alkylene-O)$_n$—H wherein the divalent alkylene radical includes the straight chain groups and the isomeric forms thereof having from 2 to 6 carbons and n is 1 to 14. The esters and polyesters are formed by reacting the glycol with either a monobasic or dibasic acid. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid.

Figure 10:
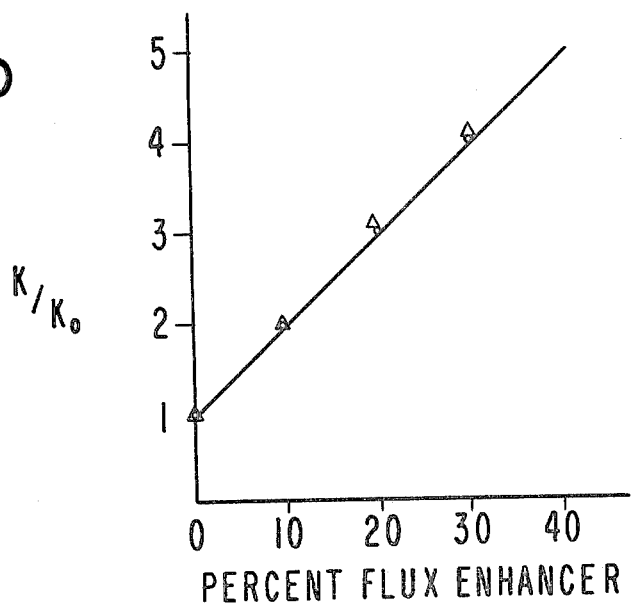
FIG. 10 represents the ratio of the fluid permeability of a semipermeable lamina containing a flux regulator compared to the fluid permeability of the same semipermeable lamina without flux regulator.

Suitable flux regulators for compounding with a semipermeable material to increase or decrease its fluid permeability can be selected by blending known amounts of a regulator with the material, casting the blends into a thin lamina, and then measuring the change in permeability towards the fluid found in the environment of use. For example, two separate batches of lamina forming cellulose acetate having an acetyl content of 32% and 39.8% were added 1, 2 and 3 grams of flux regulator polyethylene glycol having a molecular weight of 400 and the ingredients blended in a high shear blender in the presence of 120 ml of dimethyl formamide to yield six blends. Next, the blends were solvent cast with a Gardner knife and dried in an oven for 7 days at 50° C. The water permeability of the six laminae was measured in the osmosis cell described above and the results recorded in FIG. 10. In FIG. 10, the triangles represent cellulose acetate 32% and the circles represent cellulose acetate 39.8%. Also, as recorded on the ordinate, $k_o$ indicates the water permeability through cellulose acetate 32% free of flux regulator and cellulose acetae 39.8% that did not contain any flux regulator, and k indicates the water permeability through cellulose acetate 32% and cellulose acetate 39.8% where both contained the flux regulator. The positive integers 10, 20, 30 and 40 recorded on the abscissa, indicate the percent of flux regulator in the lamina. Using the above technique, specific flux regulators for blending with specific semipermeable materials to regulate the permeability can be selected for making the desired lamina for making a laminated wall. The amount of flux regulator added to a material generally is an amount sufficient to produce the desired permeability, and it will vary according to the lamina forming material and the flux regulator used to modulate the permeability. Usually from 0.001 parts up to 40 parts, or higher of flux regulator can be used to achieve the desired results, with a presently preferred range consisting of 0.1 part up to 30 parts of regulator or mixture thereof for 100 parts of lamina forming material.

Exemplary plasticizers suitable for the present purpose include plasticizers that lower the temperature of the second-order phase transition of the lamina forming material or the elastic modulus thereof, increase the workability of the lamina, its flexibility, and its permeability to fluid. Plasticizers for this purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, sulfonamides, and halogenated phenyls.

Exemplary plasticizers further include dialkyl phthalates, dicycloalkyl phthalates, diaryl phthalates and mixed alkyl-aryl phthalates as represented by dimethyl phthalate, dipropyl phthalate, di(2-ethylhexyl)phthalate, di-isopropyl phthalate, diamyl phthalate and dicapryl phthalate, alkyl and aryl phosphates such as tributyl phosphate, trioctyl phosphate, tricresyl phosphate, and triphenyl phosphate; alkyl citrate and citrate esters such as tributyl citrate, triethyl citrate, and acetyl triethyl citrate; alkyl adipates such as dioctyl adipate, diethyl adipates and di(2-methylethyl)adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate. Other plasticizers include camphor, N-ethyl-(o- and p-toulene) sulfonamide, chlorinated biphenyl, benzophenone, N-cyclohexyl-p-toulene sulfonamide, and substituted epoxides.

Suitable plasticizers can be selected for blending with the lamina forming materials by selecting plasticizers that have a high degree of solvent power for the materials, are compatible with the materials over both the processing and use temperature range, exhibit permanence as seen by a strong tendency to remain in the plasticized lamina, impart flexibility to the lamina, and are non-toxic to animals, humans, avians, fishes and reptiles. Procedures for selecting a plasticizer having the described chracteristics are disclosed in the *Encyclopedia of Polymer Science and Technology*, Vol. 10, pages 228 to 306, 1979, published by John Wiley & Sons, Inc., New York. Also, a detailed description pertaining to the measurement of plasticizer properties, including solvent parameters and compatibility, the Hildebrand solubility parameter, the Flory-Huggins interaction parameter, and the cohesive-energy density, CDE, parameter is disclosed in *Plasticization and Plasticizer Processes, Advance in Chemistry Series* 48, Chapter 1, pages 1 to 26, 1965, published by the American Chemical Society, Washington, D.C. The amount of plasticizer usually is about 0.001 part up to 20 parts, of the plasticizer for 100 parts of lamina forming material, with a presently preferred range of 0.1 part to 15 parts of plasticizer, or mixtures thereof for 100 parts of lamina forming materials.

Dispersants useful for the present purpose are those dispersants when added to a lamina aid in producing an integral composite that is useful for making the operative laminated wall of a system. The dispersants act by regulating the surface energy of materials to improve their blending into the composite. This latter material is used for manufacturing devices that maintain their integrity in the environment of use during the agent release period. Generally, the dispersants are amphipathic molecules comprised of a hydrophobic part and a hydrophilic part. The dispersants can be anionic, cationic, nonionic or amphoteric and they include anionics such as sulfated esters, amides, alcohols, ethers and carboxylic acids; sulfonated aromatic hydrocarbons, aliphatic hydrocarbons, esters and ethers; acylated amino acids and peptides; and metal alkyl phosphates; cationic dispersants such as primary, secondary, tertiary and quaternary alkylammonium salts; acylated polyamines; and salts of heterocyclic amines; arylammonium dispersants; esters of polyhdric alcohols; alkoxylated amines; polyoxyalkylene; esters and ethers of polyoxyalkylene glycols; alkanolamine fatty acid condensates; and dialkyl polyoxyalkylene phosphates; and ampholytics such as betamines; and amino acids.

Typical dispersants include polyoxyethlenated glycerol ricinoleate; polyoxyethylenated castor oil having from 9 to 52 moles of ethylene oxide; glycerol mannitan laurate, and glycerol (sorbitan oleates, stearates or laurates); polyoxyethylenated sorbitan laurate, palmitate, stearate, oleate or hexaolate having from 5 to 20 moles of ethylene oxide; mono-, di- and poly-ethylene glycol stearates, laurates, oleates, myristates, behenates or ricinoleates; propylene glycol carboxylic acid esters; sorbitan laurate, palmitate, oleate and stearate; polyoxyethylenated octyl, nonyl, decyl, and dodecylphenols having 1 to 100 moles of ethylene oxide; polyoxyethylenated nonyl; lauryl, decyl, cetyl, oleyl and stearyl alcohols having from 3 to 50 moles of ethylene oxide, polyoxypropylene glycols having from 3 to 300 moles of ethylene oxide; sodium salt of sulfated propyl oleate; sodium di(heptyl)sulfosuccinate; potassium xylene sulfonate; 1:1 myristic acid diethanolamide; N-coco-$\beta$-aminopropionic acid; bis-(2-hydroxyethyl)tallowamine oxide; (disobutyl-phenoxyethoxyethyl)dimethylbenzylammonium halide; N,N'-polyoxypropylenated ethylenediamine having a molecular weight from 500 to 3000; tetralkylammonium salts with up to 26 carbon atoms in the cation; sodium or potassium salt of polypeptide cocoanut, or oleic acid condensate; metal salts of N-acylated short chain aminosulfonic acids; soybean phosphatides; and sulfobetaine.

Suitable dispersants can be selected from the above and from other dispersants for blending with lamina forming materials by using the dipersant's hydrophile-lipophile balance number, HLB. This number represents the proportion between the weight percentages of hydrophilic and lipophilic groups in a dispersant. In use, the number indicates the behavior of the dispersant, that is, the higher the number the more hydrophilic the dispersant and the lower the number the more lipophilic the dispersant. The required HLB number for blending lamina forming materials is determined by selecting a dispersant with a known number, blending it with the materials and observing the results. A homogenous composite is formed with the correct number, while a heterogenous mixture indicates a different number is needed. This new number can be selected by using the prior number as a guide. The HLB number is known to the art for many dispersants, and they can be experimentally determined according to the procedure in *J. Soc. Cosmetic Chem.*, Vol. 1, pages 311 to 326, 1949, or it can be calculated by using the procedure in *J. Soc. Cosmetic*, Vol. 5, pages 249 to 256, 1954, and in *Am. Perfumer Essent. Oil. Rev.*, Vol. 65, pages 26 to 29, 1955. Typical HLB numbers are set forth in Table 1. Generally, a number of 10 or less indicates lipophilic behavior and 10 or more indicates hydrophilic behavior. Also, HLB numbers are algebraically additive. Thus, by using a low number with a high number, blends of dispersants can be prepared having numbers intermediate between the two numbers. Generally, the amount of dispersant will range from about 0.001 parts up to 15 parts for 100 parts of lamina forming material with a presently preferred range of 0.1 to 10 parts dispersant or mixtures thereof, for 100 parts of lamina forming material.

TABLE 1

| DISPERSANT | HLB NUMBER |
| --- | --- |
| Sorbitan trioleate | 1.8 |
| Polyoxyethylene sorbitol beeswax | 2.0 |
| Sorbitan tristearate | 2.1 |
| Polyoxyethylene sorbitol hexastearate | 2.6 |
| Ethylene glycol fatty acid ester | 2.7 |
| Propylene glycol fatty acid ester | 3.4 |
| Propylene glycol monostearate | 3.4 |
| Ethylene glycol fatty acid ester | 3.6 |
| Glycerol monostearate | 3.8 |
| Sorbitan monooleate | 4.3 |
| Propylene glycol monolaurate | 4.5 |
| Diethylene glycol fatty acid ester | 5.0 |
| Sorbitan monopalmitate | 6.7 |
| Polyoxyethylene dioleate | 7.5 |
| Polyoxypropylene mannitol dioleate | 8.0 |
| Sorbitan monolaurate | 8.6 |
| Polyoxyethylene lauryl ether | 9.5 |
| Polyoxyethylene sorbitan monolaurate | 10.0 |
| Polyoxyethylene lanolin derivative | 11.0 |
| Polyoxyethylene glycol 400 monooleate | 11.4 |
| Triethanolamine oleate | 12.0 |
| Polyoxyethylene nonyl phenol | 13.0 |
| Polyoxyethylene sorbitan monolaurate | 13.3 |
| Polyoxyethylene sorbitol lanolin | 14.0 |
| Polyoxyethylene stearyl alcohol | 15.3 |
| Polyoxyethylene 20 cetyl ether | 15.7 |
| Polyoxyethylene 40 stearate | 16.9 |
| Polyoxyethylene monostearate | 17.9 |
| Sodium oleate | 18.0 |
| Potassium oleate | 20.0 |

Microporous materials suitable for making lamina 17 of system 10 comprise preformed microporous polymeric materials and polymeric materials that can form a microporous lamina in the environment of use. The microporous materials, in both embodiments are laminated to lamina 18 to form laminated wall 12. The preformed materials suitable for forming the lamina 17 are essentially inert, they maintain their physical and chemical integrity during the period of agent release and they can be generically described as having a sponge-like appearance that provides a supporting structure for semipermeable lamina 18 and also provide a supporting structure for microscopic-sized interconnected pores or voids. The materials can be isotropic wherein the structure is homogenous throughout a cross-sectional area, or they can be anisotropic wherein the structure is non-homogenous through-out a cross-sectional area. The pores can be continuous pores that have an opening on both faces of a microporous lamina, pores interconnected through tortuous paths of regular and irregular shapes including curved, curved-linear, randomly oriented continuous pores, hindered connected pores and othre porous paths descernible by microscopic examination. Generally, microporous lamina are defined by the pore size, the number of pores, the tortuosity of the microporous path and the porosity which relates to the size and the number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used for making lamina 18. The pore size and other parameters characterizing the microporous structure also can be obtained from flow measurements, where a liquid flux, J, is produced by a pressure difference $\Delta P$, across the lamina. The liquid flux through a lamina with pores of uniform radius extended through the membrane and perpendicular to its surface with area A given by the relation 1:

$$J = \frac{N\pi r^4 \Delta P}{8\eta \Delta x} \qquad (1)$$

wherein J is the volume transported per unit time and lamina area containing N number of pores of radius r, $\eta$ is the viscosity of the liquid, and $\Delta P$ is the pressure difference across the lamina with thickness $\Delta x$. For this type of lamina, the number of pores N can be calculated from relation 2, wherein $\epsilon$ is the porosity defined as the ratio of void volume to total volume of the lamina: and A is the cross-sectional area of the lamina containing N pores.

$$N = \epsilon \times \frac{A}{\pi r^2} \qquad (2)$$

The pore radius then is calculated from relation 3:

$$r = \left( 8\eta \frac{J \cdot \Delta x \cdot \tau}{\Delta p \cdot \epsilon} \right)^{\frac{1}{2}} \qquad (3)$$

wherein J is the volume flux through the lamina per unit area produced by the pressure difference $\Delta P$ across the lamina, $\eta$, $\epsilon$ and $\Delta x$ have the meaning defined above and $\tau$ is the tortuosity defined as the ratio of the diffusional path length in the lamina to the lamina thickness. Relations of the above type are discussed in *Transport Phenomena In Membranes*, by Lakshminatayanaiah, N, Chapter 6, 1969, published by Academic Press, Inc., New York.

As discussed in this reference on page 336, in Table 6.13, the porosity of the lamina having pore radii r can be expressed relative to the size of the transported molecule having a radius a, and as the ratio of molecular radius to pore radius a/r decreases, the lamina becomes porous with respect to this molecule. That is, when the ratio a/r is less than 0.3, the lamina becomes substantially microporous as expressed by the osmotic reflection coefficient $\sigma$ which decreases below 0.5. Microporous lamina with a reflection coefficient $\sigma$ in the range of less than 1, usually from 0 to 0.5, and preferably less than 0.1 with respect to the active agent are suitable for fabricating the system. The reflection coefficient is determined by shaping the material in the form of a lamina and carrying out water flux measurements as a function of hydrostatic pressure difference and as a function of the osmotic pressure difference caused by the active agent. The osmotic pressure difference creates a hydrostatic volume flux, and the reflection coeficient is expressed by relation 4:

$$\sigma = \frac{\text{hydrostatic pressure difference} \times \text{osmotic volume flux}}{\text{osmotic pressure difference} \times \text{hydrostatic volume flux}} \quad (4)$$

Properties of microporous materials are described in *Science*, Vol. 170, pages 1302 to 1305, 1970; *Nature*, Vol. 214, pages 285, 1967; *Polymer Engineering and Science*, Vol. 11, pages 284 to 288, 1971; U.S. Pat. Nos. 3,567,809 and 3,751,536; and in *Industrial Processing With Membranes*, by Lacey R. E., and Loeb, Sidney, pages 131 to 134, 1972, published by Wiley, Interscience, New York.

Microporous materials having a preformed structure are commercially available and they can be made by art-known methods. The microporous materials can be made by etched nuclear tracking, by cooling a solution of flowable polymer below the freezing point whereby solvent evaporates from the solution in the form of crystals dispersed in the polymer and then curing the polymer followed by removing the solvent crystals, by or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes*, by R. E. Kesting, Chapters 4 and 5, 1971, published by McGraw Hill, Inc.; *Chemical Reviews*, Ultrafiltration, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos. 3,565,259; 3,615,024; 3,751,536; 3,801,692; 3,852,224; and 3,849,528.

Microporous materials useful for making the lamina include microporous polycarbonates comprised of linear polyesters of carbonic acid in which carbonate groups recur in the polymer chain, microporous materials prepared by the phosgenation of a dihydroxyl aromatic such as bisphenol a, microporous poly(vinylchloride), microporous polyamides such as polyhexamethylene adipamide, microporous modacrylic copolymers including those formed from poly(vinylchloride) 60% and acrylonitrite, styrene-acrylic and its copolymers, porous polysulfones characterized by diphenylene sulfone groups in a linear chain thereof, halogenated poly(vinylidene), polychloroethers, acetal polymers, polyesters prepared by esterification of a dicarboxylic acid or anhydride with an alkylene polyol, poly(alkylenesulfides), phenolic polyesters, microporous poly(saccharides), microporous poly(saccharides) having substituted and unsubstituted anhydroglucose units and preferably exhibiting a decrease permeability to the passage of water and biological fluids than semipermeable lamina 18, asymmetric porous polymers, cross-linked olefin polymers, hydrophobic or hydrophilic microporous homopolymers, copolymers or interpolymers having a reduced bulk density, and materials described in U.S. Pat. Nos. 3,597,752; 3,643,178; 3,654,066; 3,709,774; 3,718,532; 3,803,061; 3,852,224; 3,853,601; and 3,852,388, in British Pat. No. 1,126,849, and in *Chem. Abst.*, Vol. 71 4274F, 22572F, 22573F, 1969.

Additional microporous materials include poly(urethanes), cross-linked, chain-extended poly(urethanes), microporous poly(urethanes) in U.S. Pat. No. 3,524,753, poly(imides), poly(benzimidazoles), collodion (cellulose nitrate with 11% nitrogen), regenerated proteins, semisolid cross-linked poly(vinylpyrrolidone), microporous materials prepared by diffusion of multivalent cations into polyelectrolyte sols as in U.S. Pat. No. 3,565,259, anisotropic permeable microporous materials of ionically associated polyelectrolytes, porous polymers formed by the coprecipitation of a polycation and a polyanion as described in U.S. Pat. Nos. 3,276,589; 3,541,055; 3,541,066 and 3,546,142, derivatives of poly(styrene) such as poly(sodium styrenesulfonate) and poly(vinyl benzyltrimethyl-ammonium chloride), the microporous materials disclosed in U.S. Pat. No. 3,615,024 and U.S. Pat. Nos. 3,646,178 and 3,852,224.

Further, the microporous forming material used for the purpose of the invention, includes the embodiment wherein the microporous lamina is formed in situ, by a pore-former being removed by dissolving or leaching it to form the microporous lamina during the operation of the system. The pore-former can be a solid or a liquid. The term liquid, for this invention embraces semi-solids, and viscous fluids. The pore-formers can be inorganic or organic. The pore-formers suitable for the invention include pore-formers that can be extracted without any chemical change in the polymer. The pore-forming solids have a size of about 0.1 to 200 microns and they include alkali metal salts such as sodium chloride, sodium bromide, potassium chloride, potassium sulfate, potassium phosphate, sodium benzoate, sodium acetate, sodium citrate, potassium nitrate and the like. The alkaline earth metal salts such as calcium phosphate, calcium nitrate, and the like. The transition metal salts such as ferric chloride, ferrous sulfate, zinc sulfate, cupric chloride, manganese fluoride, manganese fluorosilicate, and the like. The pore-formers include organic compounds such as polysaccharides. The polysaccharides include the sugars sucrose, glucose, fructose, mannitol, mannose, galactose, aldohexose, altrose, talose, sorbitol, lactose, monosaccharides and disaccharides. Also, organic aliphatic and aromatic ols, including diols and polyols, as exemplified by polyhydric alcohols, poly-(alkylene glycols), polyglycols, alkylene glycols, poly-($\alpha$-$\omega$)-alkylenediols esters or alkylene glycols and the like as described above. The pore-formers are non-toxic, and on their removal from lamina 17, channels are formed through lamina 17 that fill with fluid. The channels become a diffusional path for fluid to enter reservoir 13. The paths extend from one side of lamina 17 to the other side for letting fluid into reservoir 13. In a preferred embodiment, the non-toxic pore-forming agents are selected from the group consisting of inorganic and organic salts, carbohydrates, polyalkylene glycols, poly($\alpha$-$\omega$)-alkylenediols, esters of alkylene glycols, and glycols, that are used for forming lamina 17 in a biological environment. Generally, for the purpose of this invention, when the polymer contains more than 30% by weight of a pore-former the polymer is a precursor microporous membrane that on removing the pore-formers yields a lamina which is substantially microporous, and at concentrations less than this, the membrane behaves like a semipermeable membrane.

The expression "portal" as used herein comprises means and methods suitable for releasing the agent from the system. The expression includes passageway, aperture, and orifice through the laminated wall formed by mechanical procedures, laser drilling, or by eroding an erodible element, such as a gelatin plug, in the environment of use. A detailed description of osmotic portals or passageways and the maximum and minimum dimensions for same are disclosed in U.S. Pat. Nos. 3,845,770 and 3,916,899.

The osmotically effective compounds that can be used for the purpose of the invention include inorganic and organic compounds that exhibit an osmotic pressure gradient against an external fluid across the laminated wall of the system. The compounds are used mixed with an agent or drug that has limited solubility in the external fluid with the compounds forming a salution containing agent that is osmotically delivered from the system. The phrase "limited solubility" as used herein means the agent or drug has a solubility of about less than 1% by weight in the aqueous fluid present in the environment. The osmotic solutes are used by homogenously or heterogenously mixing the solute with the agent or drug, and then changing them into the reservoir. The solutes attract fluid into the reservoir producing a solution of solute which is delivered from the system conconmitantly transporting undissolved and dissolved agent to the exterior of the system. Osmotically effective solutes used for the former purpose include magnesium sulfate, magnesium chloride, sodium chloride, lithium chloride, potassium sulfate, sodium sulfate, lithium sulfate, calcium sulfate, potassium acid phosphate, calcium lactate, d-mannitol, urea, inositol, magnesium succinate, tartaric acid, carbohydrates such as raffinose, sucrose, glucose, α-d-lactose monohydrate, and mixtures thereof.

The osmotic solute is initially present in excess and it can be in any physical form such as particle, crystal, pellet, tablet, strip, film or granule. The osmotic pressure of saturated solutions of various osmotically effective compounds and for mixtures of compounds at 37° C., in water, is listed in Table 2. In the table, the osmotic pressure $\pi$, is in atmospheres, ATM. Theosmotic pressure is measured in a commercially available osmometer that measures the vapor pressure difference between pure water and the solution to be analyzed, and according to standard thermodynamic principles, the vapor pressure ratio is converted into osmotic pressure difference. In Table 2, osmotic pressures of from 20 ATM to 500 ATM are set forth; of course, the invention includes the use of lower osmotic pressures from zero, and higher osmotic pressures than those set forth by way of example in Table 2. The osmometer used for the present measurements is identified as Model 320B, Vapor Pressure Osmometer, manufactured by the Hewlett Packard Co., Avonadale, Penna.

TABLE 2

| COMPOUND OR MIXTURE | OSMOTIC PRESSURE ATM |
| --- | --- |
| Lactose-Fructose | 500 |
| Dextrose-Fructose | 450 |
| Sucrose-Fructose | 430 |

TABLE 2-continued

| COMPOUND OR MIXTURE | OSMOTIC PRESSURE ATM |
| --- | --- |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Dextrose | 82 |
| Potassium Sulfate | 39 |
| Mannitol | 38 |
| Sodium Phosphate Tribasic . 12H$_2$O | 36 |
| Sodium Phosphate Dibasic . 7H$_2$O | 31 |
| Sodium Phosphate Dibasic . 12H$_2$O | 31 |
| Sodium Phosphate Dibsic Anhydrous | 29 |
| Sodium Phosphate Monobasic . H$_2$O | 28 |

The expression "active agent" as used herein broadly includes any compound, or mixture thereof, that can be delivered from the system to produce a beneficial result. The agent can be soluble in fluid that enters the reservoir and functions as an osmotically effective solute or it can have limited solubility in the fluid and be mixed with an osmotically effective compound soluble in fluid that is delivered from the system. The active agent includes pesticides, herbicides, germicides, biocides, algicides, rodenticides, fungicides, insecticides, antioxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility, inhibitors, fertility promoters, air purifiers, micro-organism attenuators, and other agents that benefit that environment of use.

In the specification and the accompanying claims, the term "drug" includes any physiologically or pharmacologically active substances that produce a localized or systemic effect or effects in animals, which term includes mammals, humans and primates. The term also includes domestic household, sport or farm animals such as sheep, goats, cattle, horses and pigs, for administering to laboratory animals such as mice, rats and guinea pigs, and to fishes, to avains, to reptiles and zoo animals. The term "physiologically" as used herein denotes the administration of drug to produce normal levels and functions. The term "pharmacologically" denotes variations in response to amounts of drug including therapeutics. *Stedman's Medical Dictionary*, 1966, published by Williams & Wilkins, Baltimore, Md. The phrase drug formulation as used herein means the drug is in the compartment by itself, or the drug is in the compartment mixed with an osmotic solute, binder, dye, mixtures thereof, and the like. The active drug that can be delivered includes inorganic and organic compounds without limitation, including drugs that act on the peripheral nerves, adrenergic receptors, chlolinergic receptors, nervous system, skeletal muscles, cardiovascular, smooth muscles, blood circulatory system, synoptic sites, neuroeffector junctional sites, endocrine and hormone systems, immunological system, reproductive system, skeletal system, autacoid systems, alimentary and excretory systems, inhibitory of autocoids and histamine systems, those materials that act on the central nervous system such as hypnotics and sedatives, including pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethylisovaleramide and α-bromoisovaleryl ures; hypnotic and sedative urethanes and disulfanes; psychic energizers such as isocoboxazid, nialamide, phenelzine, imipramine, tranylcypromine and parglyene; tranquilizers such as chloropromazine, promazine, fluphenazine, reserpine, deserpidine, meprobamate, and benzodiazepines such as chlordiazepoxide; anticonvulstants such as primidone, enitabas, diphenylhydantion, ethltion, pheneturide and ethosuximide; muscle relaxants and antiparkinson agents such as mephenesin, methocarbomal, trihexlphenidyl, and biperiden; anti-hypertensives such as methyl dopa and L-β-3-4-dihydroxypenhnylalanine, and pivaloyloxyethyl ester of α-methyldopa hydrochloride dihydrate; analgesics such as morphine, codeine, meperidine, nalorphine, antipyretics and anti-inflammatory agents such as aspirin, indomethacin, salicylamide, naproxen, colchicine fenoprofen, sulidac, diclofenac, indoprofen and sodium salicylamide, local anesthetics such as procaine, lidocaine, maepaine, piperocaine, tetracaine and dibucane; antispasmodics and muscle contractants such as atropine, scopolamine, methscopolamine, oxyphenonium, papaverine; prostaglandins such as $PGE_1$, $PGE_2$, $PGF_{1\alpha}$, $PGF_{2\alpha}$ and PGA; anti-microbials such as penicillin, tetracycline, oxytetracycline, chlorotetracycline, chloramphenicol and sulfonamides; anti-malarials such as 4-aminoquinolines, 8-aminoquinolines and pyrimethamine; hormonal agents such as prednisolone, cortisone, cortisol and triamcinolone; androgenic steroids such as methyltestosterone, and fluoxmesterone; estrogenic steroids such as 17β-estradiol, α-estradiol, estriol, α-estradiol 3-benzoate, and 17-ethynyl estradiol-3-methyl ether; progestational steroids such as progesterone, 19-nor-pregn-4-ene-3,20-dione, 17-hydroxy-19-nor-17-α-pregn-5(10)-ene-20-yn-3-one, 17α-ethynyl-17-hydroxy-5(10)-estren-3-one, and 9β,10α-pregna-4,6-diene-3,20-dione; sympathomimetic drugs such as epinephrine, amphetamine, ephedrine and norepinephrine; hypotensive drugs such as hydralazine; cardiovascular drugs such as procainamide, procainamide hydrochloride, amyl nitrite, nitroglycerin, dipyredamole, sodium nitrate and mannitol nitrate; diuretics such as chlorathiazide, acetazolamide, mthazolamide and flumethiazide; antisparastics such as bephenium, hydroxynaphthoate, dichlorophen and dapsone; and neoplastics such as mechlorethamine, uracil mustard, 5-fluorouracil, 6-thioguanine and procarbazine; β-blockers such as pindolol, propranolol, practolol, metoprolol, oxprenolol, timolol, atenolol, alprenolol, and acebutolol; hypoglycemic drugs such as insulin, isophane insulin, protamine zinc insulin suspension, globin zinc insulin, extended insulin zinc suspension, toblutamide, acetohexamide, tolazamide and chlorpropamide; antiulcer drugs such as cimetidine; nutritional agents such as ascorbic acid, niacin, nicotinamide, folic acid, choline, biotin, pantothenic acid, and vitamin $B_{12}$; essential amino acids; essential fats; eye drugs such as pilocarpine, pilocarpine salts such as pilocarpine nitrate, pilocarpine hydrochloride, dichlorphenamide, atropine, atropine sulfate, scopolamine and eserine salicylate; histamine receptor antagonists such as cimetidine; and electrolytes such as calcium gluconate, calcium lactate, potassium chloride, potassium sulfate, sodium chloride, potassium fluoride, sodium fluoride, ferrous lactate, ferrous gluconate, ferrous sulfate, ferrous fumurate and sodium lactate; and drugs that act on α-adrenergic receptors such as clonidine hydrochloride. The beneficial drugs are known to the art in *Remington's Pharmaceutical Sciences*, 14th Ed., 1970, published by Mack Publishing Co., Easton, Penna.; and in The *Pharmacological Basis of Therapeutics*, by Goodman and Gilman, 4th Ed., 1970, published by The MacMillian Company, London.

The drug can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides which have solubility characteristics suitable for use herein can be used alone or mixed with other drugs. Also, a drug that is water insoluble can be used in a form that is a water soluble derivative thereof to effectively serve as a solute, and on its release from the device, is converted by enzymes, hydrolyzed by body pH or other metabolic processes to the original form, or to a biologically active form. The agent can be in the reservoir as a solution, dispersion, paste, cream, particle, granule, emulsion, suspension or powder. Also, the agent can be mixed with a binder, dispersant, emulsifier or wetting agent and dyes.

The amount of agent present in the system is initially in excess of the amount that can be dissolved in the fluid that enters the reservoir. Under this physical state when the agent is in excess, the system will osmotically operate to give a substantially constant rate of release. The rate of release can also be varied by having different amounts of agent in the reservoir to form solutions containing different concentrations of agent for delivery from the device. Generally, the system can house from 0.05 ng to 5 grams or more, with individual systems containing for example, 25 ng, 1 mg, 5 mg, 125 mg, 250 mg, 500 mg, 750 mg, 1.5 g, and the like. The devices can be administered once, twice or thrice daily.

The solubility of an agent in the fluid can be determined by known techniques. One method consists of preparing a saturated solution comprising the fluid plus the agent as ascertained by analyzing the amount of agent present in a definite quantity of the fluid. A simple apparatus for this purpose consists of a test tube of medium size fastened upright in a water bath maintained at constant temperature and pressure, in which the fluid and agent are placed and stirred by a rotating glass spiral. After a given period of stirring, a weight of the fluid is analyzed and the stirring continued an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may not be needed, if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin*, No. 67 of the Hygenic Laboratory; *Encyclopedia of Science and Technology*, Vol. 12, pages 542 to 556, 1971, published by McGraw-Hill, Inc.; and *Ency-* clopedia Dictionary of Physics, Vol. 6, pages 547 to 557, 1962, published in Pergamon Press, Inc.

The systems of the invention are manufactured by standard techniques. For example, in one embodiment, the agent and other ingredients that may be housed in the compartment and a solvent are mixed into a solid, semisolid or gel form by conventional methods such as ballmilling, calendering, stirring, or rollmilling and then pressed into a preselected shape. The laminae forming the system can be applied by molding, spraying or dipping the pressed shape into wall forming materials. In another embodiment, the laminae can be cast into films, shaped to the desired dimensions, an exterior lamina sealed to an interior lamina to define a compartment that is filled with agent and then closed. The system also can be manufactured with an empty compartment that is filled through the passageway. The system when formed of more than one laminate, joined by various joining techniques such as high frequency electronic sealing that provides clean edges and firmly sealed systems. Another, and presently preferred, technique that can be used to apply laminae to a compartment is the air suspension procedure. This procedure consists in suspending and tumbling the pressed agent in a current of air and a lamina composition until the lamina is applied to the agent. The procedure is repeated with a different lamina to form the laminate. The air suspension procedure is described in U.S. Pat. No. 2,799,241; *J. Am. Pharm. Assoc.*, Vol. 48, pages 451 to 459, 1979; and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remington, Fourteenth Edition, pages 1626 to 1678, 1970, published by Mack Publishing Company, Easton, Penna.

Exemplary solvent suitable for manufacturing the laminates and laminae include inert inorganic and organic solvents that do not adversely harm the materials and the final laminated wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, buty alcohol, methyl acetate ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

The following examples are merely illustrative of the present invention, and they should not be considered as limiting the scope of the invention in any way, as these examples and other equivalents thereof will become apparent to those versed in the art in the light of the present disclosure, the drawings and the accompanying claims.

EXAMPLE 1

Figure 11:
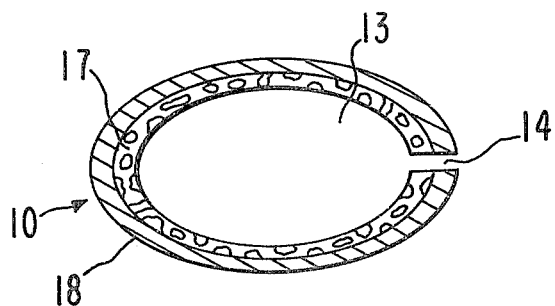
FIG. 11 is a cross-section through the osmotic system of FIG. 1, designed as an oral system; and, FIG. 12 and FIG. 13 represent the drug delivery rate ratio for osmotic systems made with a semipermeable wall compared with systems made with a microporous semipermeable laminate.

The delivery rate from an osmotic system 10 made according to the invention, which system 10 is structurally illustrated in opened section in FIG. 11 is given by equation (1), wherein dm is the mass per unit time dt.

$$\left(\frac{dm}{dt}\right)_t = \frac{A \cdot S}{R_t} \tag{1}$$

In equation 1, A is the system laminated area, S is the solubility of the agent and $R_t$ is the resistance of the laminated wall to the passage of water, which is further defined by equation (2).

$$R_t = R_1 + R_2 \tag{2}$$

In equation 2, $R_1$ is the resistance of microporous lamina 17 and $R_2$ is the resistance of semipermeable lamina 18. The resistance of $R_1$ and $R_2$ are given by equations (3) and (4) as follows:

$$R_1 = \frac{h_1}{D_1 \epsilon/\tau} \tag{3}$$

$$R_2 = \frac{h_2}{(k\pi)_2} \tag{4}$$

is the tortuosity of microporous lamina 17. In equation $(K\pi)_2$ is the water transmission rate through semipermeable lamina 18 in equation (2) and further defined by equation (5) as follows:

$$\frac{dv}{dt} = (k\pi)_2 \frac{A}{h_2} \tag{5}$$

wherein dv/dt is the volume flux through semipermeable lamina 18 of thickness $h_2$ with a surface area A.

The total delivery rate (dm/dt) from system 10 can be scientifically determined from equations (1) through (4) as given by equation (6) as follows:

$$\left(\frac{dm}{dt}\right)_t = \frac{A \cdot S}{\frac{h_1}{D_1 \epsilon/\tau} + \frac{h_2}{(k\pi)_2}} \tag{6}$$

The drug solubility S, and dimensions A, h, and $h_2$ are easily determined by procedures described above and by conventional laboratory measurements. The quantity $(k\pi)_2$ is obtained from osmosis measurement so that only the expressioin $D_1 \epsilon/\tau$ need be defined. Since the microporous lamina can be laminated onto drug reservoirs, two methods are presented which can be used to fully characterize the resistance of $R_1$.

Method 1: Determination of $R_1$ from drug diffusion experiments.

From the Stokes-Einstein relationship, *Concise Dictionary of Physics*, is known the diffusion coefficient D of molecules with radius r and molecular weight M are related by equation (7) as follows:

$$D \sim \frac{1}{1} \sim \frac{1}{M^{\frac{1}{3}}} \tag{7}$$

It follows therefore that the ratio of the diffusion coefficient of water $D_1$ to the diffusion of coefficient of drug $D_D$ is given by equation (8) as follows:

$$D_1 = D_D \left(\frac{M_D}{M_1}\right)^{\frac{1}{2}} \quad (8)$$

wherein $M_1$ is the molecular weight of water and $M_D$ is the molecular weight of the drug. By multiplying both sides of equation (8) by $\epsilon/\tau$ the relationship between the resistance of the microporous lamina to water $R_1$ and to drug $R_D$ is given by equation (9).

$$R_1 = R_D \left(\frac{M_1}{M_D}\right)^{\frac{1}{2}} \quad (9)$$

The resistance $R_D$ is calculated by measuring the zero order release rate of drug, $(dm/dt)_D$ by diffusion, from drug reservoirs laminated with a microporous lamina, expressed by equation 10 as follows:

$$\left(\frac{dm}{dt}\right)_D = D_D \cdot \frac{\epsilon}{\tau} \cdot \frac{A}{h_1} \cdot S \quad (10)$$

Here $R_D$ is defined by equation (11) as follows:

$$R_D = \frac{h_1}{D_D \epsilon/\tau} \quad (11)$$

An additional refinement of the method can be advantageously used by expressing the diffusion coefficient as a function of the molecular weight by equation (12) as seen in *Biochemica et Biophysica Acta*, Vol. 5, pages 258, 1950, as follows:

$$D = f(M) \quad (12)$$

$$f(M) = \frac{a}{M^{\frac{1}{2}}} + \frac{b}{M^{\frac{1}{3}}} + \frac{C}{M} \left(\frac{Cm^2}{sec}\right) \quad (13)$$

wherein $a = 2.74 \times 10^{-5}$, $b = 1.65 \times 10^{-5}$, $c = 17 \times 10^{-5}$. Using equation (12) rather than equation (8) results in equation (14):

$$R_1 = R_D \times \frac{f(M_1)}{f(M_D)} \quad (14)$$

wherein $R_D$ is calculated from equation (10), $f(M_1)$ and $f(M_D)$ are calculated from equations (13) and (14) by substituting the appropriate molecular weights $M_1$ and $M_D$.

Method 2. Determination of $R_1$ from the comparison of release rates from a series of microporous-semipermeable laminated walls and semipermeable laminated systems.

Figure 12:
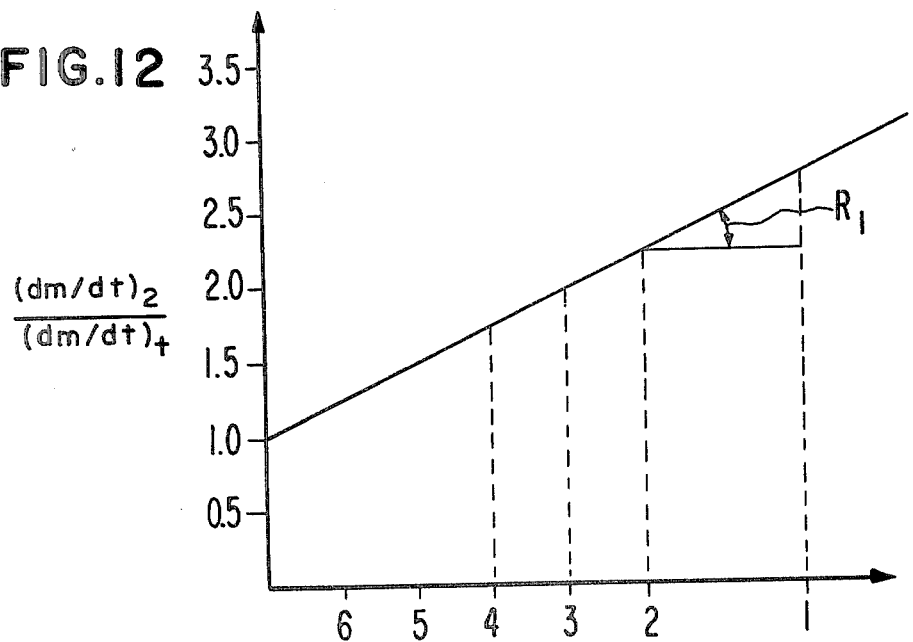

The release rate of an osmotic system manufactured only with a semipermeable wall (2) is given by equation (15) as follows:

$$\left(\frac{dm}{dt}\right)_2 = \frac{A \cdot S}{R_2} \quad (15)$$

with $$R_2 = \frac{h_2}{(K\pi)_2} \quad (16)$$

which, when compared to a system 10 with the same drug reservoir but manufactured with an additional microporous lamina 17 the ratio of rates from equations (1), (2) and (15) is given by equation (17) as follows:

$$\frac{(dm/dt)_2}{(dm/dt)_t} = 1 + \frac{R_1}{R_2} \quad (17)$$

wherein $R_1$ can be calculated from the graph illustrating $(dm/dt)_2/(dm/dt)_t$ vs $1/R_2$ as seen in FIG. 12 wherein the expression $(dm/dt)_2$ is the semipermeable lamina, $(dm/dt)_t$ is the laminated wall comprising a semipermeable and microporous lamina, the numbers on the x axis are values of $1/R_2$ indicated by sample numbers and the numbers on the y axis are the ratio of the two release rates defined by the expressions, and $R_1$ is then the slope of the straight line.

FIG. 12 is obtained as follows: therapeutic osmotic systems 10, comprising a drug reservoir surrounded with a microporous lamina, and systems 10 comprising of only a drug reservoir are laminated with a semipermeable lamina prepared in an air suspension machine, from which they are taken at successive time intervals, 1, 2, 3, etc. as seen in FIG. 12. Systems of any time interval 1, 2, 3, etc. have equal values of $R_2$. The values for $R_2$ of the successive samples 1, 2, 3, etc. are calculated from equation (15) on measuring $(dm/dt)_2$. Successive values $(dm/dt)_t$ are also measured for the laminated system having the microporous and semipermeable laminated wall, such that the ratio $(dm/dt)_2/(dm/dt)_t$ can be calculated for each value of $R_2$ and plotted as shown in FIG. 12. The resistance of the microporous lamina $R_1$ is then obtained from the slope of the straight line which intersects the ordinate at value of 1.

EXAMPLE 2

An osmotic therapeutic system for the release of the potassium chloride was made as follows: first, 500 mgs of potassium chloride was compressed by standard techniques using a ⅜ inch concave punch, to yield a compressed mass of 2.3 cm². Next, a plurality of pressed masses having a total weight of 2 kgs were placed in a Wurster air suspension coating machine with a semipermeable lamina forming solution. The lamina forming solution containing acetate having a 32% acetyl content in 2204 g of acetone:water in the ratio of 88.5:115 by weight, with the solution prepared by using high speed Waring blender. The semipermeable lamina had a thickness of 4 mils.

Next, a microporous forming lamina was laminated to the surface of the semipermeable lamina. The microporous lamina was applied from a solution prepared by mixing 48 g of cellulose acetate having an acetyl content of 32% with 32 g of sorbitol in 1520 g of acetone:water solvent having a 80:20 ratio by weight. The ingredients were mixed in a high speed blender. The microporous lmaina was applied to the system until it had a thickness of 3 mils. The osmotic systems were dried in an oven at 50° C. until the solvent was evaporated from the laminated wall.

Finally, a portal having a diameter of 10.5 mils was mechanically drilled through the 7 mil thick laminated wall to yield the osmotic system. The laminated wall maintains its physical and chemical integrity in the presence of the drug and the system has a continuous rate of release of 34 mgs per hour over a prolonged period of 14 hours.

EXAMPLE 3

A plurality of osmotic therapeutic systems are manufactured according to the procedure of Example 2, wherein the conditions are as described except that the drug of Example 2 is replaced with an orally administrable drug selected from the group consisting of methazolamide, ethoxyolamide, diazepan, amitriptylene hydrochloride, imipramine hydrochloride, nacin, benzthiazide, chorothiazide, tolbutamide, tolazamide, chloropropamide, procainamide hydrochloride, colchicine, and atropine, along with an osmotically effective solute selected from the group consisting of sodium chloride, mannitol and glucose.

EXAMPLE 4

An osmotic therapeutic system designed for orally releasing lithium sulfate is prepared according to the following parameters: (a) the water transmission rate of cellulose acetate having an acetyl content of 32% and using lithium sulfate as the osmotic driving agent is $$0.05 \frac{cm^3 \cdot mil}{cm^2 \cdot hr};$$

(b) the plasticized film of cellulose acetate having an acetyl content of 32% and a polyethylene glycol 400 content of 10% has a water transmission value with lithium sulfate as the osmotic attractant of $$0.1 \frac{cm^3 \cdot mil}{cm^2 \cdot hr};$$

(c) therefore, a 60 mg per hour release rate of lithium sulfate the wall of the system would have a thickness of $$h = \frac{A \times S \times K\pi}{dm/dt}; \text{ or } h = \frac{1.92 \times 310 \times 1}{60};$$

for a thickness of 1 mil.

Osmotic therapeutic systems having a single semipermeable wall of 1 mil thick could not endure the mechanical insult present in the environment of use and they need a supportive means. A strong, substantially rigid microporous lamina with zero resistance to water transport supports a thin semipermeable lamina and unexpectedly produce the desired delivery rate.

Next, drug reservoirs were prepared by screening a composition of 95% lithium sulfate and 5% poly(vinylpyrrolidone) in ethanol:water, 90:10 by volume, through a 30 mesh screen and then dried to remove the solvent. Then, the dried composition was passed through a 40 mesh screen and the screened product mixed with 1% magnesium stearate. Reservoirs of 400 mgs each were compressed with a 5/16 inch concave punch in a Manesty press tableting machine using the final screened composition containing the magnesium stearate. The reservoirs had an area of 1.92 cm². The desired release rate dm/dt of 60 mg/hr for systems having a semipermeable lamina of 1 mil and a microporous lamina of 5 mils is obtained by preparing the system as follows: first, 2 kg of lithium sulfate reservoirs were placed in an air suspension machine and surrounded with a microporous lamina until a 5 mil thick lamina was applied to each reservoir. The microporous lamina forming solutions was prepared by mixing 88.8 kg of cellulose acetate having an acetyl content of 38.3% with 22.2 g of polyethylene glycol and 111 g of sorbitol in acetone:water, 78.22% by weight, until a clear solution was obtained. The solvent had a final volume of 4310 ml and it consisted of 3540 ml of acetone and 770 ml of water.

To the microporous lamina was then applied a semipermeable lamina, which lamina had a thickness of 1 mil. The semipermeable lamina forming solution was prepared by blending 27 g of cellulose acetate having an acetyl content of 32% and 3 g of polyethylene glycol 400 in a high speed blender using acetone:water, 90:10, as the solvent. These polymeric solutions contained 2% solids.

The laminated osmotic systems were dried in an oven to remove the solvent, and then a 7.9 mil portal was drilled through the wall. The final systems had a controlled and continuous rate of release of 58 mgs per hour over a prolonged period of 7 hours.

EXAMPLE 5

A plurality of osmotic therapeutic systems are manufactured according to the procedure of Example 5 with all conditions as described except that the lamina forming the semipermeable lamina is replaced with a semipermeable lamina selected from the group consisting of cellulose propionate having a propionyl content of 39.5%, cellulose acetate propionate having an acetyl content of 1.5 to 7% and a propionyl content of 39 to 42%, and cellulose acetate butyrate having an acetyl content of 13 to 15% and a butyryl content of 34 to 39%. The laminates are effected by using the air suspension techniques described in *J. Pharm. Sci.*, Vol. 53, No. 8, pages 877 to 881, 1964 and ibid, Vol. 53, No. 8, pages 953 to 955, 1964.

EXAMPLE 6

A series of osmotic systems were made according to the procedure of Example 1, Method 2, to ascertain the resistance to water transport for microporous laminae. The osmotic systems were constructed for the controlled delivery of the drug acetazolamide. The systems contained drug cores of sodium acetazolamide with an equivalency of 500 mg of acetazolamide. This example also demonstrates the inventive use of microporous lamina as supporting means for semipermeable lamina used for the manufacture of operative, osmotic therapeutic systems.

The osmotic systems were made as follows: first, capsular-shaped drug cores of acetazolamide were made with and without a microporous lamina, $MP_1$. Next, the uncoated cores and the microporous lamina coated cores were coated with a semipermeable lamina $h_2$. The resistance $R_2$ for semipermeable lamina and the semipermeable microporous laminate, $R_2$, were calculated from the weight of the semipermeable lamina. The values for $h_2$ and $R_2$ are listed in Table 3.

Figure 13:
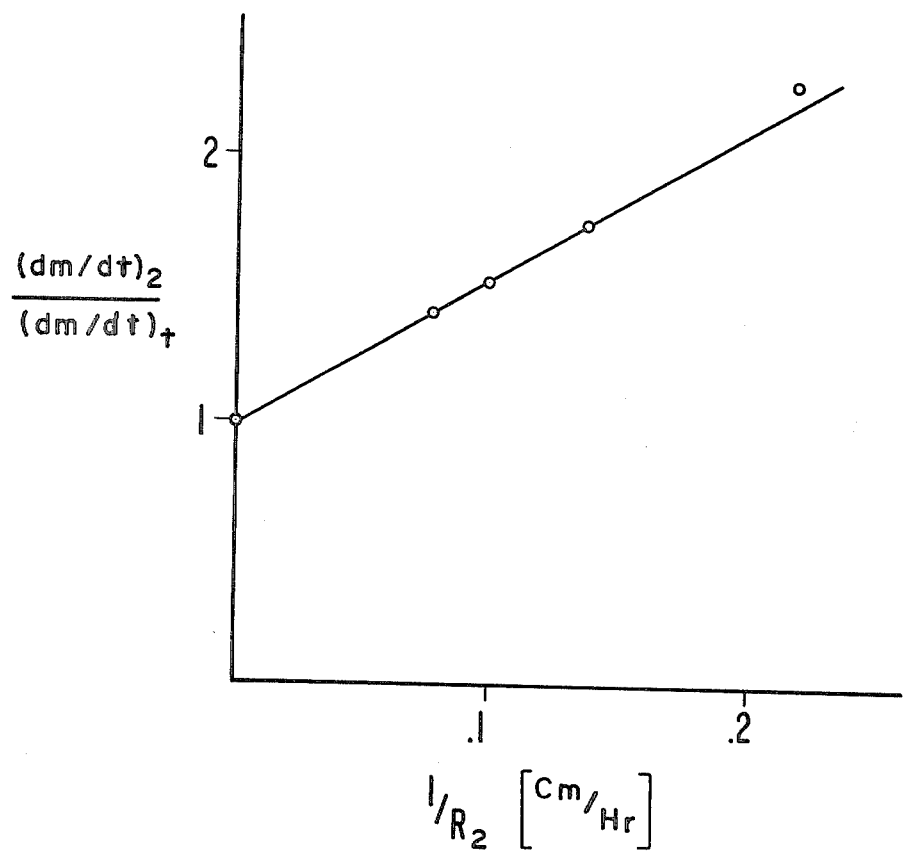

In Table 3, $(dm/dt)_2$ is the release rate for sodium acetazolamide coated with a semipermeable lamina and measured in physiological saline; $(dm/dt)_t$ is the release rate for sodium acetazolamide coated with a laminate consisting of a microporous lamina and a semipermeable lamina measured in a physiological saline; $h_1$ is the thickness of the microporous lamina, 5.14 mils; $h_2$ is the thickness of the semipermeable lamina laminated on the microporous lamina; $R_1$ is the resistance to water transport of the microporous lamina having a thickness $h_1$ of 5.14 mils wherein $R_1$ equals 5.55 hr/cm as calculated from the slope of FIG. 13. The microporous lamina of the system consisted of 55% cellulose acetate having an acetyl content of 38.3% and 45% sorbitol. The microporous lamina was coated from a solvent consisting of acetone:water, 79:21% by weight. The semipermeable lamina consisted of 58.7% cellulose acetate having an acetyl content of 32%, 26% cellulose acetate having an acetyl content of 36.3% sorbitol. The lamina was coated from the above solvent.

TABLE 3
Release Rates and Laminae Resistances To Water Transport For Drug Delivery Systems.

| $(dm/dt)_2$ mgs/hr. | $1/R_2$ (cm/hr) | $(dm/dt)_t$ mgs/hr | $h_2$ mils | $\frac{(dm/dt)_2}{(dm/dt)_t}$ |
|---|---|---|---|---|
| 100 | $7.74 \times 10^{-2}$ | 70 | 2.3 | 1.42 |
| 123 | $9.9 \times 10^{-2}$ | 80 | 1.83 | 1.53 |
| 174.7 | $13.5 \times 10^{-2}$ | 100 | 1.1 | 1.76 |
| 279 | $21.6 \times 10^{-2}$ | 120 | 0.65 | 2.32 |

EXAMPLE 7

The procedure of Example 5 is repeated in this example and all conditions are as described except that the system is sized, shaped and adapted as an ocular therapeutic system, the microporous lamina forms in situ continuous paths in the lamina, and the drug in the reservoir is replaced by a member selected from the group consisting of idoxuridine, phenylephrine, pilocarpine hydrochloride, eserine, carbachol, phospholine iodine, and demecarine bromide, each mixed with an osmotically effective solute selected from the group consisting of sodium chloride and glucose-mannitol mixture.

EXAMPLE 8

A vaginal system shaped like a tampon and suitable for releasing a vaginally administrable locally or systemically acting drug which drug exhibits an osmotic pressure gradient across a laminated wall, is made by first surrounding a drug reservoir with a 10 mil thick microporous producing lamina characterized by forming in situ a lamina having a porosity of 60% and a pore size of 0.45 microns, and then laminating to the microporous lamina a 2 mil thick semipermeable producing lamina that exhibits chemical and physical inertness in the vagina. The system has a 7 to 8 mil diameter portal for release of drug.

EXAMPLE 9

An oral system for releasing theophylline monoethanolamine over a six to seven hour therapeutic period is manufactured as follows: first, a multiplicity of compressed drug cores are formed in a conventional Manesty tableting machine for lamination. The machine uses a 5/6 inch diameter concave punch to produce cores having a hardness of about 8.4 kg as measured by a Strong-Cobb hardness tester. The cores have an area of 1.45 cm² and each core contained about 125 mg of theophylline. The cores were placed in a Wurster air suspension machine that air tumbled the cores until they are uniformly coated with a laminated wall. The laminated wall has an inner lamina facing the drug reservoir and an outer lamina distant from the reservoir of drug compartment.

The laminae are consecutively coated with the Wurster machine to form an integral, laminated wall. The inner laminae is coated from a composition comprising 116 g of cellulose acetate having an acetyl content of 38.3% homogeneously mixed with 95 g of sorbitol. The two materials were thoroughly blended and then a solvent was added consisting of 80 parts of acetone and 10 parts of water, 4298 ml of acetone and 845 ml of water were used. The inner lamina had a final thickness of 4.5 mils.

The outer lamina was permanently laminated onto the inner lamina from a semipermeable blend prepared as follows: to 34.8 g of cellulose acetate having an acetyl content of 38.3% was added 34.8 g of cellulose acetate having an acetyl content of 32% and 10% g of sorbitol and the three ingredients blended with 1520 g of acetone:water (90:10 by wt) solvent in a Waring blender until a uniform lamina forming composition was produced. The semipermeable lamina was intimately and firmly laminated to the outer surface of the microporous lamina using the air suspension technique described above.

Finally, a 10 mil exit portal was drilled through the laminated wall. The laminated osmotic system keeps its physical and chemical integrity in the test environment and in the presence of drug, and it had a continuous rate of release of 15 mgs per hour over a prolonged period of 7 hours.

EXAMPLE 10

An osmotic, therapeutic system for the oral release of theophylline monoethanolamine is made as follows: first, 1.8 kg of theophylline monoethanolamine drug cores, each having an area of 2.3 cm² and a mass of 250 mg of theophylline, were prepared by compressing the drug in a Manesty machine using a ⅜ inch diameter concave punch. The cores have a hardness of about 9 kg, as measured by a Strong-Cobb hardness tester.

The laminated wall that surrounds each drug core comprising the reservoir was manufactured as follows: first, an inner microporous lamina producing blend was made by blending 90 g of cellulose acetate having an acetyl content of 39.8% with 90 grams of sorbitol in 2820 g of acetone:water solvent, 78:22% by weight, until a workable blend was produced. The blend was applied to drug reservoirs using the air suspension machine to yield the microporous lamina having a zero resistance to the passage of water.

Next, an outer semipermeable lamina that is a rate controlling lamina and is permeable to the passage of fluid and impermeable to the passage of drug and compounds present in the environment of use was prepared by homogeneously blending 45 g of cellulose acetate having an acetyl content of 38.3%, with 45 g of cellulose acetate having an acetyl content of 32% and 10 g of d-glucitol in 2400 g of acetone:water solvent, 90:10 by weight, in a high shear blender until a homogenous blend was produced. The blend was laminated onto the exterior surface of the microporous lamina to form a semipermeable lamina 2.4 mils thick. A 10.5 mil portal was drilled through the laminated wall for releasing drug from the system. The system released 20 mgs per hour of drug over a 12 hour period.

EXAMPLE 11

An osmotic oral release of sodium acetazolamide is made as follows: first, 2 kgs of sodium acetazolamide was compressed in a Manesty machine using a 7/16 inch diameter concave punch to yield a drug core having an area of 3.36 cm². Then, the core was coated in an air suspension machine with a 7.5 mil thick microporous lamina formed from a composition comprising 115 g of cellulose acetate having an acetyl content of 38.3% and 45.1 g of sorbitol. The coat was applied by the air suspension technique yielding the microporous lamina.

Next, a semipermeable lamina was firmly coated onto the microporous lamina. The semipermeable lamina was applied from a semipermeable lamina forming a composition comprising a 42.08 g of cellulose acetate having an acetyl content of 32%, 49.35 g of cellulose acetate having an acetyl content of 38.3% and 16.16 g of d-glucitol. The lamina was formed from a solvent consisting of 2045 g of acetone:water, 90:10 by weight. The semipermeable lamina had a thickness of 0.5 mils. The system released 40 mgs per hour of drug through a 10 mil passageway over a period of 15 hours.

EXAMPLE 12

An osmotic system for the oral release of sodium acetazolamide is made as follows: first, 170 grams of sodium acetazolamide and 8.5 grams of 5% polyvinylpyrrolidone in isopropyl alcohol are blended in a v-blender for 45 minutes to produce wet granules. The granules are dried in an oven at 50° C. for 48 hours and passed through a standard No. 30 mesh sieve. Then, 1.8 grams of magnesium stearate is separately passed through the No. 30 sieve and the granules are mixed with the magnesium stearate in the blender for about 30 minutes, or until a uniform mixture is obtained. The mixture is then compressed in a conventional Manesty machine using a 5/16 inch diameter concave punch to produce drug cores. The cores have a hardness of about 9 kgs, as measured by a Strong-Cobb hardness tester. The cores contain 125 mgs of acetazolamide and have and area of 1.4 $cm^2$.

The laminated wall is prepared as follows: first, a semipermeable lamina forming blend is prepared by blending 90% cellulose acetate having and acetyl content of 38.3% and 10% polyethylene glycol having a molecular weight of 400 in sufficient acetone to produce a 5% polymeric solution. Next, an outer microporous forming lamina is prepared by blending 115 g of cellulose acetate having an acetyl content of 38.3% and 95.1 g of sorbitol in 3972 g of acetone:water solvent.

Then, the drug cores prepared above are placed in a Wurster air suspension machine. The cores are air tumbled first with the semipermeable lamina until they are coated with the inner lamina forming solution. The coated cores were dried in an oven at 50° C. for one week to evaporate the solvent. Next, the dried cores are returned to the Wurster machine and coated with the outer microporous lamina forming solution. The laminated product was dried as described. Finally, a 7.5 mil passageway was mechanically drilled through the laminated wall.

EXAMPLE 13

An osmotic system for the delivery of the nonsteroid analgesic, antiinflammatory drug sodium indomethacin trihydrate was manufactured by following the procedures detailed above. In this manufacture, a drug composition was prepared for housing in the reservoir by thoroughly blending 158 mg of potassium bicarbonate, 105.2 mg of sodium indomethacin trihydrate, which is equivalent to 86 mg of indomethacin, 8.4 mg of Povidone ®, polyvinyl pyrrolidone, and 8.4 mg of stearic acid, and then compressing the blend into a reservoir forming mass. Next, the compressed drug formulation was placed into an air suspension machine and coated with a microporous lamina forming composition. The microporous lamina composition comprises 45% by weight of cellulose acetate having an acetyl content of 39.8%, 27.5% by weight of hydroxypropyl methylcellulose and 27.5% by weight of polyethylene glycol 4000. The lamina was formed from a methylene chloride 95% ethanol solvent (80:20+wt:wt), of 5% solids. The use of potassium bicarbonate as an aid for delivering the drug is the invention of P. Wong, F. Theeuwes and P. Bonsen discloses in attorney docket ARC-668 and filed in the United States Patent and Trademark Office as U.S. patent application Ser. No. 143,644, on Apr. 25, 1980.

Next, the exterior semipermeable lamina was laminated to the microporous lamina, in the air suspension machine, from a lamina forming composition comprising 50% by weight of cellulose acetate having an acetyl content of 39.8% and 50% by weight of cellulose acetate having an acetyl content of 32%. The semipermeable lamina was applied from a solvent mixture comprising methylene chloride and 95% ethanol, 80:20, wt:wt, containing 4% solids. The system was dried as described, and a mil passageway was laser drilled through the laminated wall. The system released indomethacin at the rate of 8 mg per hour.

EXAMPLE 14

An osmotic therapeutic system for the controlled delivery of indomethacin was made by following the general procedure described above. In the present system, the reservoir housed a composition comprising 56.4% potassium bicarbonate, 37.6% sodium indomethacin trihydrate, 3.0% Povidone ® and 3.0% stearic acid for a total core weight of 280 mg. The composition following compressing, had a diameter of 7.93 mm, an area of 1.6 $cm^2$ and a density of 1.65 g/ml. The system had a laminated wall comprising an interior microporous lamina consisting of 45% by weight of cellulose acetate having an acetyl content of 38.3%, 45% by weight of sorbitol, and 10% by weight of polyethylene glycol 400. The lamina was applied from a solvent comprising methylene chloride-methanol-water, (62:35:3 by wt), 4% solid for an amount of 25 mg per core. A semipermeable lamina was laminated to the microporous lamina, which semipermeable lamina comprised 50% by weight acetyl content of 38.3% and 50% by weight of cellulose acetate having an acetyl content of 32% for an amount of 12 mg per core. The lamina was applied from a solvent that consist of methylene chloride and methanol, (80:20 by wt, 4% solids). The system had a 10 mil passageway and delivered indomethacin at the rate of 8 mg per hour.

EXAMPLE 15

The system of Example 14 was manufactured in this example wherein (a) the microporous lamina was 5 mil thick, the semipermeable lamina was 3.4 mil thick and the system had a release rate of 6 mg per hour, and (b) a system wherein the microporous lamina was 5 mil thick, the semipermeable lamina was 1.7 mil thick and the system had a release rate of 12 mg per hour.

EXAMPLE 16

An osmotic system for the controlled and continuous release of pivaloyloxyethyl ester of α-methyldopa hydrochloride dihydrate was made by following the above procedures. The system comprised a reservoir of 487.8 mg of pivaloyloxyethyl ester of α-methyldopa hydrochloride dihydrate, equivalent to 250 mg of α- methyldopa, 2.7 mg of disodium ethylenediamine tetraacetic acid, 31.4 mg of polyvinyl pyrrolidone, and 2.1 mg of magnesium stearate; the system had a laminated wall comprising (a) an interior semipermeable lamina of 3.75 mg of cellulose acetate having an acetyl content of 38.3%, 1.56 mg of hydroxypropyl methylcellulose and 0.939 mg polyethylene glycol 400 laminated to (b) an exterior microporous lamina comprising 34.7 mg of cellulose acetate having an acetyl content of 38.3%, 13.04 mg of polyethylene glycol 400 and 39.12 mg of sorbitol. The system had a 10 mil diameter passageway and release 20 mg per hour equivalent of α-methyldopa.

EXAMPLE 17

A therapeutic system is made for the delvery of pivaloyloxyethyl ester of α-methyldopa hydrochloride dihydrate by repeating the procedure of Example 16, with the system of this example having a laminated wall wherein the microporous lamina is the interior lamina and it comprises cellulose acetate having an acetyl content of 39.8%, polyethylene glycol 4000 and hydroxypropyl methylcellulose, in laminar arrangement with an exterior semipermeable lamina comprising cellulose acetate having an acetyl content of 39.8%, and a decreased amount of both hydroxypropyl methylcellulose and polyethylene glycol.

EXAMPLE 18

A series of osmotic systems were made according to the above detailed procedures for the delivery of theophylline sodium glycinate. The composition housed in the reservoir comprised 600 mg of the drug, equivalent to about 300 mg of theophylline, 24 mg of polyvinyl pyrrolidone, and 6 mg of magnesium stearate. The systems had a laminated wall, with the microporous lamina comprising 45% cellulose acetate having an acetyl content of 39.8%, 27.5% polyethylene glycol 4000 and 27.5% hydroxypropyl methylcellulose as the interior lamina, and an exterior lamina comprising 70% cellulose acetate having an acetyl content of 32%, 20% hydroxypropyl methyl cellulose and 10% polyethylene glycol 400. The systems have a coating weight of 40 mg and 10 mg for the first and second layer respectively and a 15 mil diameter passageway and deliver the drug at the rate of 25 mg per hour.

A second series of osmotic systems were made for delivering the same theophylline sodium glycinate. In this series, the reservoir composition was described immediately above, the inside lamina comprised 85% cellulose acetate having an acetyl content of 36%, 7.5% hydroxypropyl methylcellulose, and 7.5% polyethylene glycol 4000, and the exterior microporous lamina comprised 45% cellulose acetate having an acetyl content of 39.8%, 27.5% polyethylene glycol 4000, and 27.5% hydroxypropyl methylcellulose. The systems had a thickness of 1 mil and 4 mil for the two lamina respectively and a 15 mil diameter passageway and a release rate of 25 mg/hr.

EXAMPLES 20–21

A lot of osmotic systems for the delivery of oxprenolol were manufactured according to the procedures above described. The reservoirs of each system housed 288 mg of oxprenolol azelate, 5.94 mg of polyvinyl pyrrolidone and 2.97 mg of magnesium stearate. The lamina of the systems facing the reservoir comprised 45% cellulose acetate having an acetyl content of 39.8%, 27.5% hydroxypropyl methylcellulose and 27.5% polyethylene glycol 4000; the same semipermeable lamina of the system facing the environment had an acetyl content of 36% formed by blending 41.4% cellulose acetate having an acetyl content of 32% with 43.6% cellulose acetate having an acetyl content of 39.8%, 7.5% polyethylene glycol 4000, and 7.5% hydroxypropyl methylcellulose. The systems have a 4.4 mil and 1.6 mil thickness of each lamina respectively, and a 10 mil diameter passageway and deliver 18 mg per hour.

A second lot of systems were prepared with the reservoir housing a composition comprising 292 mg of oxprenolol sebacinate, 591 mg of mannitol, 34.1 mg of polyvinyl pyrrolidone, and 8.5 mg of magnesium stearate. The microporous lamina facing the reservoir comprised 45% cellulose acetate having an acetyl content of 39.8%, 27.5% hydroxypropyl methylcellulose and 27.5% polyethylene glycol 4000; and the lamina facing the environment of use comprised 41.42% cellulose acetate having an acetyl content of 32%, 43.58% cellulose acetate having an acetyl content of 39.8% and 15% hydroxypropyl methylcellulose. The systems had a thickness of 4.3 mil and 1.4 mil respectively and a 10 mil diameter and delivered 18.2% mg/hr over a prolonged period of time of 16 hours.

EXAMPLE 22

A lot of osmotic systems were manufactured for delivering the drug hydralazine hydrochloride according to the above described procedures. The reservoir of the systems housed, on the average 275 mg containing 52 mg of hydralazine hydrochloride, 215 mg of mannitol, 4 mg of hydroxypropyl methylcellulose, and 4 mg of stearic acid. The systems had a laminated wall, with the inside lamina having a weight of 6.2%±1.2 mg, and an acetyl content of about 36% formed from 42.5% cellulose acetate having an acetyl content of 38.9%, 42.5% cellulose acetate having an acetyl content of 32%, and 15% hydroxypropyl methylcellulose, laminated from 80 wt% methylene chloride and 20 wt% methanol. The exterior lamina of the system weighed 25±5 mg and comprised 32.5% cellulose acetate having an acetyl content of 32%, 32.5% cellulose acetate having an acetyl content of 39.8%, and 35% hydroxypropyl methocel, with the lamina formed from the solvent 80 wt% methylene chloride, 20 wt% methanol. The final systems were off-white to buff color, round, biconvex shaped, they had an exit portal of 0.3±0.10 mm, an average release rate of 5.1 mg per hour.

The novel osmotic systems of this invention used means for the obtainment of precise release rates in the environment of use while simultaneously maintaining the integrity of the device. While there has been described and pointed out features of the invention as applied to presently preferred embodiments, those skilled in the art will appreciate that various modifications, changes, additions, and omissions in the systems illustrated and described can be made without departing from the spirit of the invention.

I claim:

1. An osmotic therapeutic system for the controlled dispensing of a drug formulation to an animal, which system comprises:
   (a) a shaped laminated wall comprising a lamina formed of a semipermeable material permeable to the passage of an external fluid and substantially impermeable to the passage of drug formulation, and a lamina formed of a microporous material, said laminated wall surrounding and forming;

(b) a compartment containing the drug formulation which exhibits an osmotic pressure gradient across the wall, and wherein the drug is a member selected from the group of drugs that act on the peripheral and central nervous systems, adrenergic and cholinergic receptors, skeletal system, skeletal and smooth muscles, circulatory and cardiovascular systems, synoptic and neuroeffector sites, alimentary and excretory systems, endocrine, hormone, autocoid, reproductive and immunological systems; and, (c) a passageway in the laminated wall communicating with the compartment and the exterior of the osmotic system for dispensing drug from the system over a prolonged period of time.

2. The osmotic therapeutic system for the controlled dispensing of drug formulation according to claim 1, wherein the animal is a human, and the system is sized and shaped for oral administration of the drug to the gastrointestinal tract of the human.

3. The osmotic therapeutic system for the controlled dispensing of drug according to claim 1, wherein the drug is hydrazaline hydrochloride.

4. The osmotic therapeutic system for dispensing drug formulation according to claim 1, wherein in operation, when the system is in use in the animal, fluid is imbibed through the laminated wall into the compartment in a tendency towards osmotic equilibrium at a rate determined by the permeability of the wall and the osmotic pressure gradient across the wall, thereby forming a solution containing drug that is dispensed through the passageway at a controlled rate over a prolonged period of time to the animal.

5. The osmotic therapeutic system for the controlled dispensing of drug formulation according to claim 1, wherein the formulation comprises an osmotically effective solute.

6. The osmotic therapeutic system for the controlled dispensing of drug according to claim 1, wherein the drug is a $\beta$-adrenoceptor blocking drug.

7. The osmotic therapeutic system for the controlled dispensing of drug according to claim 1, wherein the drug is pindolol.

8. The osmotic therapeutic system for the controlled dispensing of drug according to claim 1, wherein the drug is propranolol.

9. The osmotic therapeutic system for the controlled dispensing of drug according to claim 1, wherein the drug is practolol.

10. The osmotic therapeutic system for the controlled dispensing of drug according to claim 1, wherein the drug is metoprolol.

11. The osmotic therapeutic system for the controlled dispensing of drug according to claim 1, wherein the drug is oxprenolol.

12. The osmotic therapeutic system for the controlled dispensing of drug according to claim 1, wherein the drug is timolol.

13. The osmotic therepeutic system for the controlled dispensing of drug according to claim 1, wherein the drug is atenolol.

14. The osmotic therapeutic system for the controlled dispensing of drug according to claim 1, wherein the drug is alprenolol.

15. The osmotic therapeutic system for the controlled dispensing of drug according to claim 1, wherein the drug is acebutolol.

16. The osmotic therapeutic system for the controlled dispensing of drug according to claim 1, wherein the drug is bupranolol.

17. The osmotic therapeutic system for the controlled dispensing of drug according to claim 1, wherein the drug is labetolol.

18. The osmotic therepeutic system for the controlled dispensing of drug according to claim 1, wherein the semipermeable lamina comprises 41.4% by weight of cellulose acetate having an acetyl content of 32%, 43.6% by weight of cellulose acetate having an acetyl content of 39.8%, 7.5% by weight of polyethylene glycol 4000 and 7.5% by weight of hydroxypropyl methylcellulose, the microporous lamina comprises 45% by weight of cellulose acetate having an acetyl content of 39.8%, 27.5% by weight of polyethylene glycol 4000, and the compartment houses 288 mg of oxprenolol azelate, 6 mg of polyvinyl pyrrolidone and 3 mg of magnesium stearate 19. The osmotic therapeutic system for the controlled dispensing of drug according to claim 1, wherein the semipermeable lamina comprises 41.4% by weight of cellulose acetate having an acetyl content of 32%, 43.6% by weight of cellulose acetate having an acetyl content of 39.8% and 15% by weight of hydroxypropyl methylcellulose, the microporous lamina comprises 45% by weight of cellulose acetate having an acetyl content of 39.8%, 27.5% by weight of hydroxypropyl methylcellulose and 27.5% by weight of polyethylene glycol, and the compartment houses 292 mg of oxprenolol sebacinate, 591 mg of mannitol, 34 mg of polyvinyl pyrrolidone and 9 mg of magnesium stearate.

20. The osmotic therapeutic system for the controlled dispensing of drug according to claim 1, wherein the drug is an antihypertensive drug.

21. The osmotic therapeutic system for the controlled dispensing of drug according to claim 1, wherein the drug is clonidine.

22. The osmotic therapeutic system for the controlled dispensing of drug according to claim 1, wherein the drug is methyldopa.

23. The osmotic therapeutic system for the controlled dispensing of drug according to claim 1, wherein the drug is an ester of $\alpha$-methyldopa.

24. The osmotic therapeutic system for the controlled dispensing of drug according to claim 1, wherein the drug is pivaloyloxyethylester of $\alpha$-methyldopa.

25. The osmotic therpeutic system for the controlled dispensing of drug according to claim 1, wherein the semipermeable lamina comprises 60% by weight of cellulose acetate having an acetyl content of 38.3%, 25% by weight of hydroxypropyl methylcellulose and 15% by weight of polyethylene glycol 400, the microporous lamina comprises 40% by weight of cellulose acetate having an average acetyl content of 38.3%, 45% by weight of sorbitol and 15% by weight of polyethylene glycol 400, and the compartment houses 487 mg of pivaloyloxyethylester of $\alpha$-methyldopa hydrochloride dihydrate, 3 mg of disodium ethylenediamine tetraacetic acid, 32 mg of polyvinyl pyrrolidone and 2 mg of magnesium stearate.

26. The osmotic therapeutic system for the controlled dispensing of drug according to claim 1, wherein the semipermeable lamina comprises 60% by weight of cellulose acetate having an average acetyl content of 38.3%, 25% by weight of hydroxypropyl methylcellulose and 15% by weight of polyethylene glycol 400, a microporous lamina comprising 40% by weight cellulose acetate having an average acetyl content of 38.3%, 15% by weight of hydroxypropyl methylcellulose and 45% by weight of sorbitol, and the compartment houses 487 mg of pivaloyloxyethylester of α-methyldopa hydrochloride dihydrate, 3 mg of disodium ethylenediamine tetraacetic acid, 31 mg of polyvinyl pyrrolidone and 2.1 mg of magnesium stearate.

27. The osmotic therapeutic system for the controlled dispensing of drug according to claim 1, wherein the drug is hydralazine.

28. The osmotic therapeutic system for the controlled dispensing of drug according to claim 1, wherein the semipermeable lamina comprises 42.5% by weight of cellulose acetate having an acetyl content of 39.8%, 42.5% by weight of cellulose acetate having an acetyl content of 32% and 15% by weight of hydroxypropyl methylcellulose, the microporous lamina comprises 32.5% by weight of cellulose acetate having an acetyl content of 32%, 32.5% by weight of cellulose acetate having an acetyl content of 39.8% and 35% by weight of hydroxypropyl methylcellulose, and the compartment houses 50 mg of hydralazine hydrochloride, 214 mg of mannitol, 1 mg of hydroxypropyl methylcellulose and 1 mg of magnesium stearate.

29. The osmotic therapeutic system for the controlled dispensing of drug according to claim 1, wherein the drug is a hormone and autocoid synthesis inhibitor.

30. The osmotic therapeutic system for the controlled dispensing of drug according to claim 1, wherein the drug is an anti-inflammatory drug.

31. The osmotic therapeutic system for the controlled dispensing of drug according to claim 1, wherein the drug is indomethacin.

32. The osmotic therapeutic system for the controlled dispensing of drug according to claim 1, wherein the drug is diclofenac.

33. The osmotic therapeutic system for the controlled dispensing of drug according to claim 1, wherein the drug is sulindac.

34. The osmotic therapuetic system for the controlled dispensing of drug according to claim 1, wherein the drug is naproxen.

35. The osmotic therapeutic system for the controlled dispensing of drug according to claim 1, wherein the drug is fenoprofen.

36. The osmotic therapeutic system for the controlled dispensing of drug according to claim 1, wherein the drug is aspirin.

37. The osmotic therapeutic system for the controlled dispensing of drug according to claim 1, wherein the semipermeable lamina comprises 50% by weight of cellulose acetate having an acetyl content of 39.8% and 50% by weight of cellulose acetate having an acetyl content of 32%, a microporous lamina comprising 45% by weight of cellulose acetate having an acetyl content of 39.8%, 27.5% by weight of polyethylene glycol 4000 and 27.5% by weight of hydroxypropyl methylcellulose, and the compartment houses 105 mg of sodium indomethacin trihydrate, 8.5 mg of polyvinyl pyrrolidone, and 8.5 mg of stearic acid.

38. The osmotic therapeutic system for the controlled dispensing of drug according to claim 1, wherein the semipermeable lamina comprises 50% by weight of cellulose acetate having an acetyl content of 32% and 50% by weight of cellulose acetate having an acetyl content of 38.3%, a microporous lamina comprising 45% by weight of cellulose acetate having an acetyl content of 38.3%, 45% by weight of sorbitol and 10% by weight of polyethylene glycol 4000, and the compartment houses 105 mg of sodium indomethacin trihydrate, 8.4 mg of polyvinyl pyrrolidone and 8.4 mg of stearic acid.

39. The osmotic therapeutic system for the controlled dispensing of drug according to claim 1, wherein the drug is a histamine receptor antagonist.

40. The osmotic therapeutic system for the controlled dispensing of drug according to claim 1, wherein the drug is cimetidine.

41. The osmotic therapeutic system for the controlled dispensing of drug according to claim 1, wherein the semipermeable lamina comprises 41.4% by weight of cellulose acetate having an acetyl content of 32%, 43.6% by weight of cellulose acetate having an acetyl content of 39.8%, 7.5% by weight of hydroxypropyl methylcellulose and 7.5% by weight of polyethylene glycol, a microporous lamina comprising 45% by weight of cellulose acetate having an acetyl content of 39.8%, 27.5% by weight of polyethylene glycol 4000, and 27.5% by weight of hydroxypropyl methylcellulose, and the compartment houses 600 mg of theophylline sodium glycinate, 24 mg of polyvinyl pyrrolidone and 6 mg of magnesium stearate.

42. The osmotic therapeutic system for the controlled dispensing of drug according to claim 1, wherein the drug is terbutaline.

43. The osmotic therapeutic system for the controlled dispensing of drug according to claim 1, wherein the drug is valporate.

44. The osmotic therapeutic system for the controlled dispensing of drug according to claim 1, wherein the semipermeable lamina comprises two different cellulose polymers.

45. The osmotic therapeutic system for the controlled dispensing of drug according to claim 1, wherein the microporous lamina contains a non-toxic pore-former.

46. An osmotic therapeutic system for the controlled dispensing of a beneficial formulation to an animal, wherein the system comprises:

(a) a shaped laminated wall comprising a semipermeable lamina permeable to the passage of an external fluid and substantially impermeable to the passage of drug formulation, and a lamina formed of a microporous material having a plurality of micropores with micropaths through the lamina, said micropores having a reflection coefficient of less than 1, from 5 to 95% micropores of from 10 angstroms to 100 micron size, and a flux through the micropores expressed by:

$$J = \frac{N\pi r^4 \Delta P}{8\eta \Delta x \zeta}$$

wherein J is the volume transported per unit of lamina area having N number of micropores of radius N, $\zeta$ is the tortuosity, $\eta$ is the viscosity of the fluid in the micropores, and $\Delta P$ is the pressure difference across the lamina with thickness $\Delta x$, said laminated wall surrounding and forming:

(b) a compartment housing the drug formulation, wherein the drug is a member selected from the group consisting of anticonvulsant, antiparkinson, analgesics, hormonal, diuretic, opthalmic, tranquilizer, hypoglycemic, anti-infective, antipyretic, and psychic energizer drugs, (d) wherein in operation, when the system is in the animal and dispensing drug, fluid therefrom is imbibed through the laminated wall into the compartment, thereby forming a solution of drug formulation that is dispersed through the passageway at a controlled rate over a prolonged period of time.

47. The osmotic therapeutic system for the controlled dispensing of drug according to claim 46, wherein the system is sized and adapted for placement in the eye and the compartment houses timolol.

48. The osmotic therapeutic system for the controlled dispensing of drug according to claim 46, wherein the system is sized and adapted for placement in the eye, and the drug in the compartment is an opthalmic β-adrenergic blocker.

49. The osmotic therapeutic system for the controlled dispensing of drug according to claim 46, wherein the system is sized and adapted for placement in the eye and the compartment houses the opthalmic drug metoprolol.

50. The osmotic therapeutic system for the controlled dispensing of drug according to claim 46, wherein microporous lamina has a surface area A with a plurality of pores according to the following relation:

$$N = \epsilon \frac{A}{r^2 \times 3.14}$$

wherein N is the number of pores and $\epsilon$ is the porosity, A the area of the lamina, and r the pore radius.

51. A method for the controlled administration of a drug formulation to the gastrointestinal tract of a human, which method comprises:

A. admitting orally into the gastrointestinal tract an osmotic therapeutic system comprising:
  (1) a shaped laminated wall comprising a lamina formed of a semipermeable material that is permeable to the passage of drug formulation, and a lamina made of a material that forms a microporous lamina in the gastrointestinal tract, which microporous lamina comprises a plurality of micropores having a reflection coefficient of less than 1, said laminated wall surrounding and forming:
  (2) a compartment containing the drug formulation that exhibits an osmotic pressure gradient across the wall;
  (3) a passageway in the wall communicating with the compartment and the exterior of the system for administering drug from the system; and, B. administering drug to the gastrointestinal tract by imbibing fluid through the wall into the compartment, thereby forming a solution containing drug that is dispensed through the passageway at a controlled rate in a therapeutically effective amount over a prolonged period of time.

52. The method for the controlled administration of the drug according to claim 51, wherein the microporous lamina formed in the gastrointestinal tract comprises a plurality of micropores with paths through the microporous lamina, said micropores exhibiting a reflection coefficient of less than 1, the microporous lamina having from 5 to 95% micropores of from 10 angstroms to 100 microns in size, and a fluid flux through the micropores of:

$$J = \frac{N\pi r^4 \Delta P}{8\eta \Delta x}$$

wherein J is the fluid volume transported per unit time, said microporous lamina having N number of micropores of radius r, $\eta$ is the viscosity of the fluid and $\Delta P$ is the pressure difference across the semipermeable lamina with a thickness $\Delta X$.

53. The method for the controlled administration of drug formulation according to claim 51, wherein the material that forms a microporous lamina contains a pore-former that is leached from the material in the gastrointestinal tract.

54. The method for the controlled administration of drug according to claim 51, wherein the microporous lamina is formed during operation of the system be leaching a pore-former present in the material, and the formed microporous lamina has a surface area A and a plurality of pores according to the following relation:

$$N = \epsilon \frac{A}{r^2 \times 3.14}$$

wherein N is the number of pores and $\epsilon$ is the porosity, and r the pore radius.

55. The method for the controlled administration of drug according to claim 51, wherein the microporous lamina is formed in the gastrointestinal tract by leaching from the microporous forming material a souble pore-former, and the micropores formed by leaching the pore-former have a radius of:

$$r = \left(8\eta \frac{J \cdot \Delta x \cdot \tau}{\Delta P \cdot \epsilon}\right)^{\frac{1}{2}}$$

wherein J is the volume flux, $\eta$ is the viscosity of the liquid, $\epsilon$ is the porosity, $\Delta P$ is the pressure difference across the lamina, $\Delta x$ is the thickness of the lamina and $\tau$ is the tortuosity.

56. The method for the controlled administration of drug according to claim 51, wherein the drug formulation comprises a drug and an osmotically effective solute.

57. The method for the controlled administration of drug according to claim 51, wherein the drug in the compartment is indomethacin.

58. The method for the controlled administration of drug according to claim 51, wherein the drug in the compartment is pivaloyloxyethylester of α-methyldopa hydrochloride dihydrate.

59. The method for the controlled administration of drug according to claim 51, wherein the drug in the compartment is cimetidine.

60. The method for the controlled administration of drug according to claim 51, wherein the drug in the compartment is oxprenolol.

61. The method for the controlled administration of drug according to claim 51, wherein the drug in the compartment is metoprolol.

62. The method for the controlled administration of drug according to claim 51, wherein the drug in the compartment is propranolol.

63. The method for the controlled administration of drug according to claim 51, wherein the drug in the compartment is hydralazine.

64. The method for the controlled administration of drug according to claim 51, wherein the drug in the compartment is clonidine.

65. The method for the controlled administration of drug according to claim 51, wherein the drug in the compartment is sulindac.

66. The method for the controlled administration of drug according to claim 51, wherein the drug in the compartment is naproxen.

* * * * *